US010753952B2

(12) United States Patent
Reisinger

(10) Patent No.: US 10,753,952 B2
(45) Date of Patent: *Aug. 25, 2020

(54) RAPID AND SENSITIVE METHOD OF FORENSIC TOXICOLOGY IN POST-MORTEM SUBJECTS AND IN LIVE AND POST-MORTEM ANIMALS USING ORAL FLUID TESTING

(71) Applicant: Amy J. Reisinger, Venetia, PA (US)

(72) Inventor: Amy J. Reisinger, Venetia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/390,884

(22) Filed: Apr. 22, 2019

(65) Prior Publication Data

US 2019/0250178 A1 Aug. 15, 2019

Related U.S. Application Data

(63) Continuation-in-part of application No. 15/785,703, filed on Oct. 17, 2017, now Pat. No. 10,267,811, which is a continuation-in-part of application No. 15/164,402, filed on May 25, 2016, now Pat. No. 9,817,006, which is a continuation-in-part of application No. 14/744,324, filed on Jun. 19, 2015, now Pat. No. 9,366,685.

(51) Int. Cl.
*G01N 33/94* (2006.01)
*G01N 30/72* (2006.01)
*C40B 30/10* (2006.01)
*G01N 30/04* (2006.01)
*A61B 10/00* (2006.01)

(52) U.S. Cl.
CPC ......... *G01N 33/9486* (2013.01); *G01N 30/04* (2013.01); *G01N 30/72* (2013.01); *G01N 33/94* (2013.01); *G01N 33/9466* (2013.01); *A61B 10/0051* (2013.01); *G01N 33/946* (2013.01); *G01N 33/948* (2013.01); *G01N 33/9426* (2013.01)

(58) Field of Classification Search
CPC ................................ C40B 30/10; G01N 33/94
See application file for complete search history.

(56) References Cited

U.S. PATENT DOCUMENTS

| | | | | |
|---|---|---|---|---|
| 2010/0190190 | A1* | 7/2010 | Dodds | G01N 33/6854 435/7.92 |
| 2011/0195402 | A1* | 8/2011 | Selinfreund | A61B 10/0045 435/6.1 |
| 2015/0346170 | A1* | 12/2015 | Huang | G01N 30/84 436/500 |
| 2016/0025752 | A1* | 1/2016 | Santiago | G08C 17/02 436/501 |

OTHER PUBLICATIONS

Heltsley et al., Oral Fluid Drug Testing of Chronic Pain Patients. II. Comparison of Paired Oral Fluid and Urine Specimens, Journal of Analytical Toxicology, 2012, 36, 75-80. (Year: 2012).*
Cone et al., Interpretation of Oral Fluid Tests for Drugs of Abuse, Annals of New York Academy of Sciences, 2007, 1098, 51-103. (Year: 2007).*
Drummer et al., Requirements for Bioanalytical Procedures in Postmortem Toxicology, Anal. Bioanal. Chem, 2007, 388, 1495-1503. (Year: 2007).*
Josefsson, Determination of Methylphenidate and Ritalinic Acid in Blood, Plasma & Oral Fluid From Adolescents & Adults Using Protein Precipitation and Liquid Chromatography Tandem Mass Spectrometry—A Method Applied on Clinical & Forensic Investigations, J of Pharm & Biomed Anal, 2011, 55, 1050-1059. (Year: 2011).*
Chen et al., Simple LC-MS/MS Screening and Quantification Methods for the Analysis of 41 Common Pain Drugs in an Oral Fluid Matrix, AB SCIEX, 2012, 1-4. (Year: 2012).*
United Nations, Guidelines for Testing Drugs Under International Control in Hair, Sweat and Oral Fluid, United Nations Office on Drugs and Crime, 2014, 1-85. (Year: 2014).*
Horner, M., The Passage of Drugs Into Horse Saliva and the Suitability of Saliva for Pre-Race Testing, British Journal of Sports Medicine, 1976, 133-194. (Year: 1976).*
AB SCIEX, A Rapid iMethod Test for Drugs of Abuse Screening, AB SCIEX, 2010, 1-6. (Year: 2010).*

* cited by examiner

*Primary Examiner* — Amy M Bunker
(74) *Attorney, Agent, or Firm* — Acker Wood IP Law; Gwen R. Acker Wood

(57) ABSTRACT

The present invention provides a rapid, sensitive method for forensic drug testing in a post-mortem subject or a live or a post-mortem animal using oral fluid collected from the post-mortem subject or live or post-mortem animal. The method comprises collecting a sample of oral fluid from a post-mortem subject or a live or a post-mortem animal, analyzing the oral fluid sample qualitatively to detect the presence of one or more non-naturally occurring drugs, analyzing the oral fluid sample quantitatively to determine concentration of the one or more non-naturally occurring drugs in the post-mortem subject or in the live or the post-mortem animal, and identifying the one or more non-naturally occurring drugs in the post-mortem subject or in the live or the post-mortem animal. The detection and quantification in oral fluid is more sensitive and faster than detection and quantification of the non-naturally occurring drugs in blood, urine, bile, and liver tissue collected from the same post-mortem subject. Further, the qualitative and quantitative results are obtained in as little as three hours.

7 Claims, 28 Drawing Sheets

RAPID AND SENSITIVE METHOD OF FORENSIC TOXICOLOGY IN POST-MORTEM SUBJECTS AND IN LIVE AND POST-MORTEM ANIMALS USING ORAL FLUID TESTING

CROSS REFERENCE TO RELATED APPLICATIONS

This application is a continuation-in-part of application Ser. No. 15/785,703, filed Oct. 17, 2017, which is a continuation-in-part of U.S. Pat. No. 15,164,402, filed May 25, 2016, now U.S. Pat. No. 9,817,006, which is a continuation-in-part of application Ser. No. 14/744,324, filed Jun. 19, 2015, now U.S. Pat. No. 9,366,685, which is a continuation-in-part of application Ser. No. 15/785,703, filed Oct. 17, 2017 (now U.S. Pat. No. 10,267,811), all of which are incorporated by reference herein in their entirety.

FIELD OF THE INVENTION

The present invention relates to forensic toxicology in post-mortem subjects. More particularly, the present invention relates to a rapid and sensitive method of drug testing in post-mortem subjects and live and post-mortem animals using oral fluid collected from the subjects or animals to quickly and sensitively detect the presence of, and quantify the concentrations of, one or more drugs in the subjects or animals.

BACKGROUND OF THE INVENTION

In recent years, overdose from both licit and illicit drugs has been an increasingly common cause of death in persons fifteen to seventy years of age. After a suspected drug death, a major objective at autopsy is to determine whether any drugs measured in the decedent have played a role in the cause of death. Currently, post-mortem forensic drug analyses rely upon traditional biological matrices such as blood, urine, bile, and liver tissue. The specific matrix used for specimen retrieval depends, in part, on the time after death that the sample is collected and the consistency of collection, which may vary due to differences in clotting time, fluid movement and changes in cellular components. Once death has taken place, many drugs are released from their binding sites in tissue as pH decreases and the process of autolysis proceeds. By the time a sample has reached the clinical chemistry laboratory for analysis, it may be unsuitable for analysis. For example, drug concentrations in blood taken from an individual at one site may be twice the concentration as that taken at the same time from a different site (e.g., sublingual region versus femoral vein). In addition, in decaying cadavers, viable sample matrices typically are hard to retrieve and oftentimes are limited solely to putrefactive fluid in pleural cavities and blisters. Sample collection from blood, urine and body tissues also requires the use of protective gear to prevent possible spread of infection. Further, sample analyses typically are time-consuming, as various instrumentalities usually are employed for both qualitative and quantitative analyses of the samples.

Further, methods to detect and quantify non-naturally occurring drugs in live and post-mortem animals have long been needed. The number of animals that inadvertently ingest, or intentionally have been given, licit or illicit drugs has risen through the years. Currently, urine testing has been successful to detect barbiturates, opiates, benzodiazepines, and amphetamines/methamphetamines in dogs. However, urine testing is not able to quantify the concentration of these and other non-naturally occurring drugs in animals.

There exists a need, therefore, for a fast, sensitive, and less invasive method to conduct forensic toxicology in post-mortem subjects, as well as in live and post-mortem animals, than what is currently available.

SUMMARY OF THE INVENTION

The present invention fulfills this need by providing a rapid, sensitive, and less invasive method of forensic drug testing to detect and quantify non-naturally occurring drugs in post-mortem subjects, as well as in live and post-mortem animals, using oral fluid collected from post-mortem subjects and from live and post-mortem animals.

In an aspect of the invention, the method comprises collecting a sample of oral fluid from a post-mortem subject, analyzing the oral fluid sample qualitatively to detect the presence of one or more non-naturally occurring drugs, analyzing the oral fluid sample quantitatively to determine concentration of the one or more non-naturally occurring drugs in the post-mortem subject, and identifying the one or more non-naturally occurring drugs in the post-mortem subject, wherein detection and quantification in oral fluid is more sensitive and faster than detection and quantification of the non-naturally occurring drugs in blood, urine, bile, and liver tissue collected from the same post-mortem subject using the same qualitative and quantitative methods, and wherein qualitative and quantitative results are obtained in as little as three hours.

In another aspect of the invention, the method comprises collecting a sample of oral fluid from a live or post-mortem animal, analyzing the oral fluid sample to detect the presence of and quantify the concentration of the one or more non-naturally occurring drugs in the live or post-mortem animal, and identifying the one or more non-naturally occurring drugs in the live or post-mortem animal, wherein detection and quantification in oral fluid is more sensitive and faster than detection and quantification of the non-naturally occurring drugs in urine and blood, collected from the same live or post-mortem animal using the same quantitative methods, and wherein detection and quantification are obtained in as little as three hours. In an embodiment of the invention, the animal is a dog, cat, horse, or any other farm animal. In another embodiment of the invention, the animal is a dog.

The one or more non-naturally occurring drugs and drug metabolites that may be detected and quantified in accordance with the present invention includes, without limitation, drugs included in the following drug classes: non-steroidal anti-inflammatory drugs (NSAIDs) including, without limitation, acetaminophen and aspirin; alcohol; alcohol metabolites including, without limitation, ethyl glucuronide (EtG) and ethyl sulfate (EtS); barbiturates including, without limitation, amobarbital, butabarbital, butalbital, pentobarbital, phenobarbital and secobarbital; benzodiazepines including, without limitation, alprazolam, alpha-hydroxyalprazolam, oxazepam, 7-aminoclonazepam, diazepam, nordiazepam, midazolam, triazolam, temazepam, lorazepam and clonazepam; synthetic cannabinoids including, without limitation, "K2" or "spice;" cathinones including, without limitation, methylenedioxypyrovalerone (MDPV), methylone or mephedrone and Mitragyna speciose; general anesthetics including, without limitation, ketamine and norketamine; muscle relaxants including, without limitation, carisoprodol, cyclobenzaprine and meprobamate; neuroleptics including, without limitation, gabapentin and pregabalin; opiates including, without limitation, codeine, hydrocodone, hydromorphone, morphine, oxycodone, pentazocine and oxymorphone; semi-synthetic opioids including, without limitation, buprenorphine, fentanyl, meperidine, methadone, propoxyphene, o-desmethyl-cis-tramadol, tramadol and naltrexone; opioid antagonists/analgesics including, without limitation, naloxone and tapentadol; stimulants including, without limitation, amphetamine and methylphenidate; hypnotics including, without limitation, zopiclone, zolpidem and zaleplon; antitussives including, without limitation, dextromethorphan; antidepressants including, without limitation, nortriptyline and amitriptyline; cannabinoids including, without limitation, delta-9-tetrahydrocannabinol (THC); antipsychotics including, without limitation, quetiapine; anticonvulsants including, without limitation, phenytoin and lamotrigine; antihistamines including, without limitation, diphenylhydramine; and illicit drugs including, without limitation, cocaine/benzoylecgonine, heroin/6-acetylmorphine, 3,4-methylenedioxymethamphetamine (MDMA), methylenedioxyamphetamine (MDA), 3,4-methylenedioxy-N-ethylamphetamine (MDEA), methamphetamine and phencyclidine (PCP).

The sample of oral fluid is collected from either the buccal (i.e., oral) cavity of the post-mortem subject or the live or post-mortem animal, such as from the sublingual region (i.e., under the tongue), or from the submandibular region, such as the submandibular gland. Approximately one milliliter (mL) of oral fluid easily is collected in about one minute to about ten minutes using a collection pad.

After collection of the oral fluid sample, it is analyzed qualitatively using an enzyme-linked immunosorbent assay (ELISA); and is analyzed quantitatively using liquid chromatography-mass spectrometry/mass spectrometry (LC-MS/MS).

BRIEF DESCRIPTION OF THE DRAWINGS

A fuller understanding of the invention can be gained from the following description when read in conjunction with the accompanying drawings, in which.

DETAILED DESCRIPTION OF THE INVENTION

Figure 1:
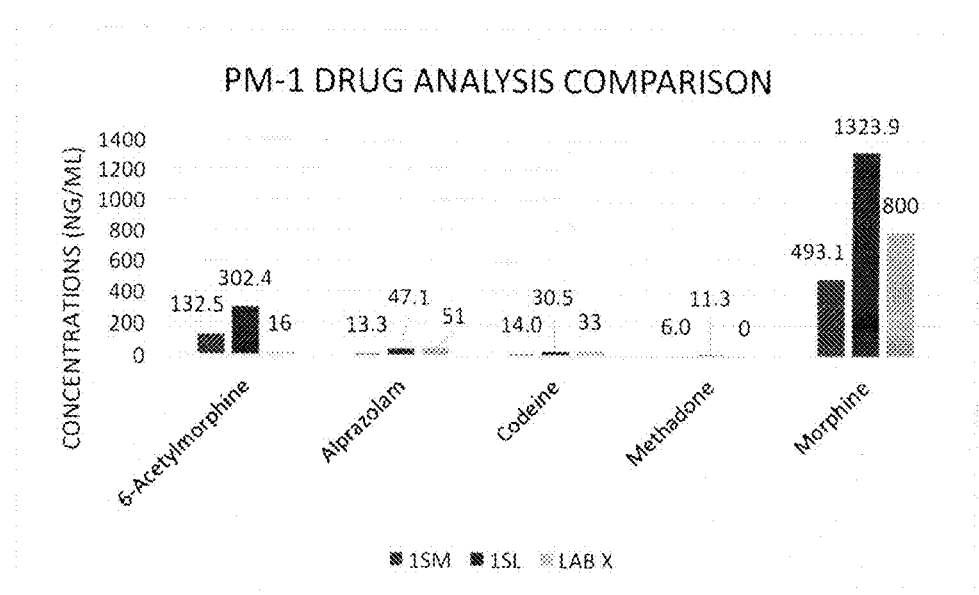
FIG. 1 is a bar graph showing concentrations of 6-acetylmorphine, alprazolam, codeine, methadone, and morphine collected from oral fluid of a post-mortem subject (PM-1) in accordance with an embodiment of the invention, compared to concentrations of the same drugs detected in blood from this subject reported by Lab X.

The following investigation was a prospective and controlled study of twenty autopsy cases from post-mortem subjects designed in order to document the efficacy, accuracy, and rapidity of using oral fluid to detect the presence of (i.e., screen) and quantify drug concentrations in forensic autopsies compared to conventional collection modalities used in forensic autopsies, which use blood, urine, bile, and liver tissue. In addition, an investigation was undertaken to document the efficacy, accuracy and rapidity of using oral fluid to quantify drug concentrations in six live dogs and in two post-mortem dogs.

As used herein, the term "post-mortem subject" is defined as a human being.

As used herein, the term "analytes" refers to all non-naturally occurring drugs except alcohol and alcohol metabolites.

Materials and Methods
Chemicals and Reagents

Chemical and certified reference standards required for analysis were purchased from Cerilliant (Round Rock, Tex.): acetaminophen, acetaminophen-$d_4$, 6-acetylmorphine, 6-acetylmorphine-$d_3$, alprazolam, alprazolam-$d_5$, amphetamine, amphetamine-$d_5$, benzoylecgonine, benzoylegonine-$d_3$, buprenorphine, buprenorphine-$d_4$, carisoprodol, carisoprodol-$d_7$, clonazepam, clonazepam-$d_4$, codeine, codeine-$d_3$, cyclobenzaprine, cyclobenzaprine-$d_3$, dextromethorphan, dextromethorphan-$d_3$, diazepam, diazepam-$d_5$, ethyl glucuronide (EtG), EtG-$d_5$, ethyl sulfate (EtS), EtS-$d_5$, fentanyl, fentanyl-$d_5$, gabapentin, gabapentin-$d_{10}$, hydrocodone, hydrocodone-$d_3$, hydromorphone, hydromorphone-$d_3$, ketamine, ketamine-$d_5$, lorazepam, lorazepam-$d_4$; meperidine-$d_4$, methylenedioxyamphetamine, methylenedioxyamphetamine-$d_5$, 3,4-methylenedioxy-N-ethylamphetamine, 3,4-methylenedioxy-N-ethylamphetamine-$d_5$, 3,4-methylenedioxymethamphetamine, 3,4-methylenedioxymethamphetamine-$d_5$, meperidine, meperidine-$d_4$, methadone, methadone-$d_3$, methamphetamine, methamphetamine-$d_5$, methylphenidate, methylphenidate-$d_9$, midazolam, midazolam-$d_4$, morphine, morphine-$d_3$, naloxone, naloxone-$d_5$, naltrexone, naltrexone-$d_3$, nortriptyline, nortriptyline-$d_3$, o-desmethyl-cis-tramadol, o-desmethyl-cis-tramadol-$d_6$, oxazepam, oxazepam-$d_5$, oxycodone, oxycodone-$d_3$, oxymorphone, oxymorphone-$d_3$, propoxyphene, propoxyphene-$d_5$, phencyclidine, phencyclidine-$d_5$, pentazocine, quetiapine, quetiapine-$d_5$, tapentadol, tapentadol-$d_3$, temazepam, temazepam-$d_5$, delta-9-tetrahydrocannabinol (delta-9-THC), detal-9-THC-$d_3$, tramadol, tramadol-$d_4$, triazolam, triazolam-$d_4$, zaleplon, zaleplon-$d_4$, zolpidem, zolpidem-$d_6$, zopiclone and zopiclone-$d_4$.

Synthetic negative saliva, ELISA kits, STOP solution, 3,3',5,5'-Tetramethylbenzidine (TMB) solution, and oral fluid multi-analyte calibrator/control sets were purchased from Immunalysis Corporation (Pomona, Calif.). Methanol (MeOH), acetonitrile, 2-propanol, and ammonium formate were purchased from Fisher Scientific (Bridgewater, N.J.). Formic acid was purchased from Acros Organics (Bridgewater, N.J.). Types 1 and 2 water were obtained from a deionized (DI) water system (Millipore).

Preparation, Sampling, and Storage Conditions of Oral Fluid

Fifteen cases of suspected drug overdose investigations were performed by CHW & Pathology Associates, Inc. at Carlow University's morgue in Pittsburgh, Pa. One case of suspected drug overdose investigation was performed in Carroll County, Carrollton, Ohio; one in Montour County, Danville, Pa.; two in Columbiana County, Lisbon, Ohio; and one in Rusk County, Ladysmith, Wis. A Pathology Assistant carefully recorded on a chain of custody form the decedent identification (ID), sex, age, weight, date, time, and location of collections. Samples of oral fluid were collected from sublingual and submandibular sites utilizing the Quantisal Saliva Collection Device (Immunalysis Corporation). In the submandibular location, the collection pad was inserted into the submandibular gland until saturation occurred. For the sublingual location, the collection pad was placed under the tongue in the buccal cavity. Table 1 provides decedent demographics for twenty subjects, and oral fluid site of collection [i.e., sublingual ("SL") or submandibular ("SM")] by our laboratory, compared to the sample (i.e., matrix source) used by a major clinical forensic toxicology laboratory, referred to herein as "Lab X."

TABLE 1

Decedent Demographics and Sample Matrices

| Decedent ID | Gender | Age | Weight | Lab X Matrix Source | Location ID | Decomposed |
|---|---|---|---|---|---|---|
| PM-1 | M | 55 | 165 | Peripheral Blood and Urine | SL, SM | |
| PM-2 | M | 44 | 350 | Peripheral Blood and Urine | SL, SM | |
| PM-3 | F | 62 | 145 | Peripheral Blood | SL, SM | |
| PM-4 | M | 33 | 180 | Peripheral Blood | SL, SM | |
| PM-5 | M | 21 | 258 | Hospital Blood | SL, SM | |
| PM-6 | M | 23 | 135 | Peripheral Blood Urine | SL, SM | |
| PM-7 | M | 67 | 175 | Peripheral Blood | SL, SM | |
| PM-8 | F | 42 | 180 | Peripheral Blood and Urine | SL, SM | |
| PM-9 | F | 43 | 160 | Peripheral Blood and Urine | SL, SM | |
| PM-10 | F | 45 | 100 | Peripheral Blood | SL | |
| PM-11 | M | 53 | 240 | Peripheral Blood and Urine | SL | Yes |
| PM-12 | F | 27 | 140 | Peripheral Blood | SL, SM | |
| PM-13 | M | 57 | 170 | Bile | SM | Yes |
| PM-14 | M | 43 | 185 | Liver Tissue | SM | |
| PM-15 | F | 39 | 120 | Peripheral Blood, Bile, and Urine | SM | |
| PM-16 | M | N/A | N/A | Subclavical Blood and Urine | SL | |
| PM-17 | M | N/A | N/A | Blood (Unknown) | SL | |
| PM-18 | M | N/A | N/A | Subclavical Blood, Vitreous, and Urine | SL | |
| PM-19 | M | N/A | N/A | Autopsy Blood | SL | |
| PM-20 | M | N/A | N/A | Autopsy Blood | SL | |

N/A—Not/Available

Each collection device was labeled with the appropriate sample location ID and date of collection. Each collection pad was placed into the appropriate sample location and observed for saturation of the pad for approximately two to ten minutes. After each sample was collected, the unmodified fluid was placed into the appropriate collection device, which contained a non-azide buffer to preserve the collected oral fluid. The chain of custody form and collection devices were individually placed into a dual-pocketed biohazard bag and transported to our laboratory to be stored in a refrigerator (2 to 8° C.) until analysis was conducted.

After the samples were prepared for analysis, they were individually bagged and labelled with the laboratory's sample ID and date of receipt. Samples were stored frozen in a freezer (−15 to −20° C.) for as long as six months for potential medico-legal purposes.

Preparation of Standard, Internal Standard, and Quality Control Solutions for Analytes All standard and internal reference standards were purchased from Cerilliant Corporation. A stock standard solution was prepared by pipetting 50 microliters (μL) of 1.0 milligram per milliliter (mg/mL) of standard analyte(s) and diluting them with MeOH to prepare a total volume of 25 mL. A stock internal standard solution was prepared by pipetting 750 μL of the 100 micrograms per milliliter (μg/mL) of internal standard analyte(s) and diluting the solution with MeOH to prepare a total volume of 150 mL. Three sets of Quality Control (QC) stock solutions were made to prepare three different concentrations: 10, 50, and 200 nanograms per milliliter (ng/mL). The 200 ng/mL QC stock solution was prepared by transferring 25 mL of stock standard solution into a graduated cylinder and diluting with synthetic negative saliva to prepare a total volume of 1 liter (L). The 10 ng/mL and 50 ng/mL QC stock solutions were prepared by serial dilutions from the 200 ng/mL QC stock solution.

Preparation of Standard, Internal Standard, and Quality Control Solutions for Alcohol All standard and internal reference standards were purchased from Cerilliant Corporation. A stock standard solution was prepared by pipetting 100 microliters (μL) of 1.0 milligram per milliliter (mg/mL) of standard analyte(s) and diluting them with MeOH to prepare a total volume of 10 mL. A stock internal standard solution was prepared by pipetting 250 μL of the 100 micrograms per milliliter (μg/mL) of internal standard analyte(s) and diluting the solution with MeOH to prepare a total volume of 50 mL. Three sets of Quality Control (QC) stock solutions were made to prepare three different concentrations: 250, 500, and 1,000 nanograms per milliliter (ng/mL). The QC solution was prepared by serial dilutions utilizing SNS to prepare a total volume of 1 mL for each concentration from the 10,000 ng/mL reference standard stock solution for the following concentrations: 2,000 ng/mL, 1,000, 500, and 250 ng/mL.

Qualitative Conditions and Methodology for ELISA

The first fifteen samples were screened on a TECAN Freedom EVO 150 (Tecan Group Ltd.). The following drug classes were analyzed: amphetamine, methamphetamine, opiates, propoxyphene, PCP, cocaine/benzoylecgonine, THC, benzodiazepines, tramadol, methadone, buprenorphine, fentanyl, oxycodone/oxymorphone, carisoprodol, and meperidine. ELISA kits (Immunalysis Corporation) were utilized to qualitatively screen for the presence of analytes. The Immunalysis Direct ELISA kit (96-well microplate) is based upon competitive binding to the antibody of enzyme-labeled antigen and unlabeled antigen in proportion to their concentration in the reaction mixture. Samples and calibrators were prepared by pipetting 750 μL into labeled 12×75 millimeter (mm) disposable glass culture tubes (Fisher Scientific). Calibrators were prepared in duplicate (negative, low, cut-off, and high).

A 10 µL aliquot of diluted sample and calibrators were incubated with a 100 µL of enzyme (horseradish peroxidase) into the microplate wells coated with fixed amounts of high affinity purified polyclonal antibody. The microplates were incubated for 60 minutes at ambient temperature (20 to 25° C.). Plates were washed six times with DI water utilizing a microplate washer (TECAN). Plates were inverted and dried onto an absorbent paper towel to remove any residual moisture. One hundred (100) µL of chromogenic substrate TMB was added. The microplates were incubated for 30 minutes at ambient temperature and the reaction was stopped after 30 minutes by adding 100 µL of dilute acid (STOP solution). The plates were read with an absorbance reader (TECAN Sunrise Absorbance Reader with Magellan Software) between wavelengths of 450 to 620 nanometers (nm).

Quantitative Conditions and Methods for LC-MS/MS

All samples were analyzed utilizing a 6460 Triple Quadrupole LC-MS/MS coupled with a 1290 Infinity Liquid Chromatography System (Agilent Technologies). The column was a Poroshell 120 EC-C18 (3.0×50 mm, 2.7 µm), maintained at 50° C. with a flow rate of 0.6 mL/minute. The column for alcohol, i.e., ethyl glucuronide (EtG) or ethyl sulfate (EtS) was a Polaris 3 C18-Ether (150×3.0 mm) maintained at 40° C. with a flow rate of 0.5 mL/minute.

The aqueous mobile phase (A) for all analytes except alcohol consisted of 5 millimolar (mM) ammonium formate and 0.1% formic acid diluted to 2 L utilizing type 1 DI water; and the organic mobile phase (B) consisted of 0.1% formic acid diluted to 2 L utilizing acetonitrile. The gradient performed is shown in Table 2.

The aqueous mobile phase (A) for alcohol consisted of 0.1% formic acid diluted to 1,998 mL 2 L utilizing type 1 DI water. The gradient performed is shown in Table 3.

TABLE 2

HPLC Gradient Program for Analytes

| Time (minutes) | % A | % B |
| --- | --- | --- |
| 0 | 95 | 5 |
| 1 | 95 | 5 |
| 3 | 70 | 30 |
| 6 | 30 | 70 |
| 6.5 | 5 | 95 |
| 7 | 99.5 | 0.5 |
| 8 | 99.5 | 0.5 |

TABLE 3

HPLC Gradient Program for Alcohol

| Time (minutes) | % A | % B |
| --- | --- | --- |
| 0 | 100 | 0 |
| 3.50 | 85 | 15 |
| 3.60 | 2 | 98 |
| 5 | 2 | 98 |
| 6 | 2 | 98 |

The injection volume for the samples was 2.5 µL. Mass spectrometry was performed utilizing a positive electrospray ionization mode for all analytes except alcohol. The source parameters were a gas ($N_2$) temperature of 300° C., gas flow of 12 L/minute nebulizer pressure of 45 parts per square inch (psi), sheath gas temperature of 350° C., and sheath gas flow of 12 L/minute. The ideal multiple-reaction monitoring (MRM) transitions, fragmentor voltages, collision energy voltages, and cell accelerator voltages were determined for all analytes (deuterated and non-deuterated) by utilizing Agilent MassHunter Qualitative Analysis and Optimizer software (installed with Agilent MassHunter software). The MRM transitions and parameters are shown in Table 4.

The injection volume for the alcohol samples was 20 µL. Mass spectrometry was performed utilizing a negative electrospray ionization mode for all analytes. The source parameters were a gas ($N_2$) temperature of 300° C., gas flow of 6 L/minute nebulizer pressure of 40 parts per square inch (psi), sheath gas temperature of 400° C., and sheath gas flow of 12 L/minute. The ideal multiple-reaction monitoring (MRM) transitions, fragmentor voltages, collision energy voltages, and cell accelerator voltages were determined for all analytes (deuterated and non-deuterated) by utilizing Agilent MassHunter Qualitative Analysis and Optimizer software (installed with Agilent MassHunter software). The MRM transitions and parameters are shown in Table 4.

TABLE 4

Analytes and Alcohol with Associated Voltages for Mass Spectrometry

| Analyte | MRM Transition (m/z) | Fragmentor Voltage (V) | Collision Energy (V) | Cell Accelerator Voltage (V) | Retention Time (min) |
| --- | --- | --- | --- | --- | --- |
| Acetaminophen | 152→110 | 117 | 15 | 7 | 1.29 |
|  | 152→93 | 117 | 20 | 7 |  |
| Acetaminophen-$D_4$ | 156.2→113.8 | 100 | 16 | 7 | 1.29 |
| 6-acetylmorphine | 328.4→165.1 | 170 | 44 | 4 | 2.35 |
|  | 328.4→152.1 | 170 | 80 | 4 |  |
| 6-acetylmorphine-$D_3$ | 331.4→165.1 | 145 | 40 | 4 | 2.35 |
| Alprazolam | 309.1→205.1 | 170 | 48 | 4 | 4.56 |
|  | 309.1→151.1 | 170 | 72 | 4 |  |
| Alprazolam-$D_5$ | 314.1→210.1 | 165 | 44 | 4 | 4.56 |
| Amphetamine | 136.2→119.1 | 70 | 4 | 4 | 2.20 |
|  | 136.2→91.0 | 70 | 20 | 4 |  |
| Amphetamine-$D_5$ | 141.2→124.1 | 75 | 8 | 4 | 2.20 |
| Benzoylecgonine | 290.3→168.1 | 135 | 16 | 4 | 2.71 |
|  | 290.3→105.0 | 135 | 32 | 4 |  |

TABLE 4-continued

Analytes and Alcohol with Associated Voltages for Mass Spectrometry

| Analyte | MRM Transition (m/z) | Fragmentor Voltage (V) | Collision Energy (V) | Cell Accelerator Voltage (V) | Retention Time (min) |
|---|---|---|---|---|---|
| Benzoylecgonine-$D_3$ | 293.3→77.1 | 135 | 68 | 4 | 2.71 |
| Buprenorphine | 468.6→115.1 | 215 | 144 | 4 | 4.16 |
| | 468.6→101.1 | 215 | 44 | 4 | |
| Buprenorphine-$D_4$ | 473.6→473.3 | 215 | 8 | 4 | 4.16 |
| Carisoprodol | 261.3→176.1 | 75 | 4 | 4 | 4.52 |
| | 261.3→158.1 | 75 | 4 | 4 | |
| Carisoprodol-$D_7$ | 268.3→183.2 | 80 | 4 | 4 | 4.52 |
| Clonazepam | 316.1→214.1 | 165 | 40 | 4 | 4.47 |
| | 316.1→151.1 | 165 | 88 | 4 | |
| Clonazepam-$D_4$ | 320.1→218.1 | 130 | 36 | 4 | 4.47 |
| Codeine | 300.1→152.1 | 165 | 76 | 4 | 2.10 |
| | 300.1→115.1 | 165 | 88 | 4 | |
| Codeine-$D_3$ | 303.4→152.1 | 150 | 80 | 4 | 2.10 |
| Cyclobenzaprine | 276.1→215.1 | 135 | 48 | 4 | 4.36 |
| | 276.1→213.1 | 135 | 88 | 4 | |
| Cyclobenzaprine-$D_3$ | 279.1→215.1 | 120 | 48 | 4 | 4.36 |
| Dextromethorphan | 272.4→171.1 | 135 | 40 | 7 | 3.93 |
| | 272.4→128.1 | 135 | 72 | 7 | |
| Dextromethorphan-$D_3$ | 275.4→128.1 | 105 | 72 | 7 | 3.93 |
| Diazepam | 285.1→193.1 | 160 | 32 | 4 | 5.19 |
| | 285.1→165.1 | 160 | 56 | 4 | |
| Diazepam-$D_5$ | 290.1→198.1 | 170 | 32 | 4 | 5.19 |
| EtG | 221.1→85 | 110 | 12 | 5 | 3.68 |
| | 221.1→75 | 110 | 12 | 5 | |
| EtG-$D_5$ | 226.1→75 | 110 | 12 | 5 | 3.56 |
| EtS | 125→96.9 | 90 | 14 | 5 | 3.31 |
| | 125→80 | 90 | 34 | 5 | |
| EtS-$D_5$ | 130→98 | 90 | 14 | 5 | 3.31 |
| Fentanyl | 337.5→188.1 | 130 | 20 | 4 | 3.86 |
| | 337.5→105.1 | 130 | 48 | 4 | |
| Fentanyl-$D_5$ | 342.5→105.1 | 135 | 48 | 4 | 3.86 |
| Gabapentin | 172.2→154.1 | 80 | 8 | 7 | 2.17 |
| | 172.2→55.1 | 80 | 24 | 7 | |
| Gabapentin-$D_{10}$ | 182.3→164.2 | 95 | 12 | 7 | 2.17 |
| Hydrocodone | 300.4→171.1 | 155 | 40 | 4 | 2.43 |
| | 300.4→128.0 | 155 | 76 | 4 | |
| Hydrocodone-$D_3$ | 303.4→128.1 | 160 | 68 | 4 | 2.43 |
| Hydromorphone | 286.3→157.1 | 180 | 44 | 4 | 1.17 |
| | 286.3→128.1 | 180 | 68 | 4 | |
| Hydromorphone-$D_3$ | 289.3→157.1 | 150 | 44 | 4 | 1.17 |
| Ketamine | 238.1→220.1 | 105 | 11 | 7 | 2.9 |
| | 238.1→125.1 | 105 | 11 | 7 | |
| Ketamine-$D_5$ | 242.1→129 | 102 | 15 | 7 | 2.9 |
| Lorazepam | 321.1→303 | 136 | 8 | 7 | 4.52 |
| | 321.1→275.1 | 136 | 21 | 7 | |
| Lorazepam-$D_4$ | 325.1→77.9 | 115 | 104 | 7 | 4.52 |
| Methylenedioxyamphetamine | 180.1→162.7 | 75 | 4 | 7 | 2.42 |
| | 180.1→76.9 | 75 | 44 | 7 | |
| Methylenedioxyamphetamine-$D_5$ | 185.1→168.1 | 83 | 5 | 7 | 2.42 |
| 3,4-Methylenedioxy-N-ethylamphetamine | 208.1→16.1 | 107 | 9 | 7 | 2.77 |
| | 208.1→105.1 | 107 | 25 | 7 | |
| 3,4-Methylenedioxy-N-ethylamphetamine-$D_5$ | 213.2→105.1 | 120 | 30 | 7 | 2.77 |
| 3,4-methylenedioxy-methamphetamine | 194.3→163.1 | 80 | 12 | 4 | 2.46 |
| | 194.3→105.1 | 80 | 24 | 4 | |
| 3,4-methylenedioxy-methamphetamine-$D_5$ | 199.3→165.1 | 55 | 12 | 4 | 2.46 |
| Meperidine | 248.3→174.1 | 115 | 16 | 4 | 3.32 |
| | 248.3→103.1 | 115 | 48 | 4 | |
| Meperidine-$D_4$ | 252.3→105.1 | 125 | 44 | 4 | 3.32 |
| Methamphetamine | 150.2→119.1 | 65 | 8 | 4 | 2.41 |
| | 150.2→91.1 | 65 | 20 | 4 | |
| Methamphetamine-$D_5$ | 155.2→121.2 | 80 | 8 | 4 | 2.41 |
| Methadone | 310.4→265.2 | 100 | 8 | 4 | 4.53 |
| | 310.4→105.1 | 100 | 24 | 4 | |
| Methadone-$D_3$ | 313.4→268.1 | 110 | 12 | 4 | 4.53 |
| Methylphenidate | 235.2→84.1 | 100 | 16 | 7 | 3.18 |
| | 235.2→56.1 | 116 | 53 | 7 | |
| Methylphenidate-$D_9$ | 244.3→93.1 | 120 | 16 | 7 | 3.18 |
| Midazolam | 326.1→248.6 | 155 | 40 | 7 | 4.02 |
| | 326.1→221.9 | 155 | 52 | 7 | |

TABLE 4-continued

Analytes and Alcohol with Associated Voltages for Mass Spectrometry

| Analyte | MRM Transition (m/z) | Fragmentor Voltage (V) | Collision Energy (V) | Cell Accelerator Voltage (V) | Retention Time (min) |
|---|---|---|---|---|---|
| Midazolam-$D_4$ | 330.1→249 | 167 | 40 | 7 | 4.02 |
| Morphine | 286.3→165.1 | 155 | 48 | 4 | 0.82 |
|  | 286.3→152.1 | 155 | 68 | 4 |  |
| Morphine-$D_3$ | 289.3→152.1 | 170 | 72 | 4 | 0.82 |
| Naloxone | 328.2→310.1 | 120 | 16 | 7 | 2.13 |
|  | 328.2→212.1 | 120 | 40 | 7 |  |
| Naloxone-$D_5$ | 333.4→212.1 | 135 | 40 | 7 | 2.13 |
| Naltrexone | 342.2→324.1 | 142 | 20 | 7 | 2.45 |
|  | 342.2→55.2 | 142 | 40 | 7 |  |
| Naltrexone-$D_3$ | 345.2→58 | 105 | 44 | 7 | 2.45 |
| Nortriptyline | 264.3→202 | 105 | 60 | 7 | 4.51 |
|  | 264.3→91 | 105 | 24 | 7 |  |
| Nortriptyline-$D_3$ | 267.4→91 | 105 | 24 | 7 | 4.51 |
| o-desmethyl-cis-tramadol | 250.8→232.1 | 110 | 12 | 4 | 2.44 |
|  | 250.8→58.2 | 110 | 12 | 4 |  |
| o-desmethyl-cis-tramadol-$D_6$ | 256.8→64.2 | 110 | 12 | 4 | 2.44 |
| Oxazepam | 287.1→163.0 | 120 | 40 | 4 | 4.38 |
|  | 287.1→104.1 | 120 | 36 | 4 |  |
| Oxazepam-$D_5$ | 292.1→109.1 | 110 | 40 | 4 | 4.38 |
| Oxycodone | 316.4→298.1 | 135 | 16 | 4 | 2.31 |
|  | 316.4→212.1 | 135 | 44 | 4 |  |
| Oxycodone-$D_3$ | 319.4→115.1 | 125 | 104 | 4 | 2.31 |
| Oxymorphone | 302.3→198.1 | 130 | 44 | 4 | 0.96 |
|  | 302.3→128.1 | 130 | 88 | 4 |  |
| Oxymorphone-$D_3$ | 305.3→201.2 | 125 | 48 | 4 | 0.96 |
| Phencyclidine | 244.3→159.2 | 80 | 8 | 4 | 3.74 |
|  | 244.3→117.1 | 80 | 32 | 4 |  |
| Phencyclidine-$D_5$ | 249.3→164.2 | 80 | 8 | 4 | 3.74 |
| Pentazocine* | 286.4→218.1 | 135 | 16 | 4 | 3.57 |
|  | 286.4→145.1 | 135 | 36 | 4 |  |
| Propoxyphene | 340.5→266.2 | 80 | 4 | 4 | 4.49 |
|  | 340.5→128.0 | 80 | 56 | 4 |  |
| Propoxyphene-$D_5$ | 345.5→271.2 | 80 | 4 | 4 | 4.49 |
| Quetiapine | 384.3→220.6 | 145 | 40 | 7 | 4.03 |
|  | 384.3→138.8 | 145 | 96 | 7 |  |
| Quetiapine-$D_8$ | 392.2→258.1 | 122 | 20 | 7 | 4.03 |
| Tapentadol | 222.8→108.1 | 130 | 24 | 4 | 3.13 |
|  | 222.8→121.0 | 120 | 15 | 4 |  |
| Tapentadol-$D_3$ | 225.8→77.1 | 120 | 52 | 4 | 3.13 |
| Temazepam | 301.1→283.1 | 120 | 8 | 4 | 4.78 |
|  | 301.1→255.1 | 120 | 20 | 4 |  |
| Temazepam-$D_5$ | 306.1→260.1 | 120 | 20 | 4 | 4.78 |
| $\Delta^9$-THC | 315→193 | 150 | 20 | 7 | 7.2 |
|  | 315→123 | 150 | 30 | 7 |  |
| $\Delta^9$-THC-$D_3$ | 318.4→196.3 | 125 | 20 | 7 | 7.2 |
| Tramadol | 264.3→58.2 | 90 | 16 | 7 | 3.15 |
|  | 264.3→42.2 | 90 | 112 | 7 |  |
| Tramadol-$D_4$ | 268.4→58.2 | 90 | 16 | 7 | 3.15 |
| Triazolam | 343.1→308 | 190 | 24 | 7 | 4.65 |
|  | 343.1→239 | 190 | 44 | 7 |  |
| Triazolam-$D_4$ | 347.1→312 | 195 | 28 | 7 | 4.65 |
| Zaleplon | 306.3→64.1 | 135 | 80 | 7 | 4.21 |
|  | 306.3→43.1 | 135 | 60 | 7 |  |
| Zaleplon-$D_4$ | 310.3→65.1 | 135 | 92 | 7 | 4.21 |
| Zolpidem | 308.3→26.3 | 100 | 20 | 7 | 3.46 |
|  | 308.3→235.2 | 100 | 20 | 7 |  |
| Zolpidem-$D_6$ | 313.9→235.1 | 100 | 30 | 7 | 3.46 |
| Zopiclone | 389.8→146.1 | 80 | 16 | 7 | 3.05 |
|  | 389.8→112 | 80 | 64 | 7 |  |
| Zopiclone-$D_4$ | 393.8→246.1 | 80 | 8 | 7 | 3.05 |

*The internal standard for pentazocine was unavailable for purchase. Therefore, meperidine-$D_4$ was utilized as the internal standard.

Sample Preparation

All samples, except alcohol samples, were filtered from the collection pad in the Quantisal collection device. This was conducted via a blood serum filter (16 mm×4 inches) (Porex Technologies). Five-hundred µL of each sample was pipetted into a LC-MS/MS vial (Fisher Scientific) with 120 µL of MeOH and 30 µL of stock internal standard solution. Alcohol samples were prepared by pipetting 540 µL of sample with 60 µL of stock internal standard solution. Alcohol samples were prepared by pipetting 540 µL of sample with 60 µL of stock internal standard solution. After addition of the solutions, the vial was capped and vortexed for approximately 10 seconds.

Method Validation

Both instruments (TECAN Freedom Evoware 150 and Agilent 6460 Triple Quadrupole LC-MS/MS coupled with a 1290 Infinity Liquid Chromatography System) were validated utilizing the Scientific Working Group for Forensic Toxicology (SWGTOX) Standard Practices for Method Validation in Forensic Toxicology. Parameters for qualitative testing (TECAN) were validated for limit of detection and precision. Parameters for quantitative testing (LC-MS/MS) were validated for bias, calibration model, carryover, interference studies, limit of detection, limit of quantitation, The Oral Fluid Alcohol Reference Standard (STD) Stock Solution is prepared at a 10,000 ng/mL standard concentration. The 2,000 ng/mL standard concentration is prepared utilizing the 10,000 ng/mL standard concentration; the 500 ng/mL standard concentration is prepared utilizing the 2,000 ng/mL; and the 50 ng/mL standard concentration is prepared utilizing the 500 ng/mL standard concentration.

TABLE 6

Preparation of Calibration Curve Concentrations for Alcohol

| | Oral Fluid Alcohol Concentration (ng/mL) | | | | | | | |
|---|---|---|---|---|---|---|---|---|
| | 5 | 10 | 25 | 50 | 100 | 250 | 500 | 1000 |
| Diluted Oral Fluid Alcohol Reference Standard (STD) Stock Solution (μL) @ 2000 ng/mL | | | | | | | 62.5 | 125 |
| *Diluted Oral Fluid Alcohol Reference Standard (STD) Stock Solution (μL) @ 500 ng/mL | / | / | / | 25 | 50 | 125 | | / |
| **Diluted Oral Fluid Alcohol Reference Standard (STD) Stock Solution (μL) @ 50 ng/mL | 25 | 50 | 125 | / | / | / | / | / |
| SNS | 875 | 850 | 775 | 875 | 850 | 775 | 838.5 | 775 |
| Oral Fluid Alcohol ISTD (μL) | 100 | 100 | 100 | 100 | 100 | 100 | 100 | 100 |

Key
*Diluted Oral Fluid Alcohol Reference Standard (STD) Stock Solution @ 500 ng/mL = 750 μL of negative oral fluid + 250 μL of diluted Oral Fluid Reference Standard (STD) Stock Solution @ 2,000 ng/mL = 1000.0 μL = 1.0 mL
**Diluted Oral Fluid Alcohol Reference Standard (STD) Stock Solution @ 50 ng/mL = 900 μL of negative oral fluid + 100 μL of diluted Oral Fluid Reference Standard (STD) Stock Solution @ 500 ng/mL = 1000.0 μL = 1.0 mL
/ = Not Applicable precision, dilution integrity, ionization suppression/enhancement, and processed sample stability.

Calibration Curve

A calibration curve was prepared to identify the unknown concentrations of analytes in oral fluid by comparing them to a known set of concentrations. The concentrations for the calibration curve were 1, 5, 10, 50, 100, 250, 500, and 1,000 ng/mL. The concentrations were chosen based upon cut-offs for the analytes (see Table 4). The calibration curve samples were prepared as shown in Table 5.

TABLE 5

Preparation of Calibration Curve Concentrations for Analytes

| | Oral Fluid Concentration (ng/mL) | | | | | | | |
|---|---|---|---|---|---|---|---|---|
| | 1 | 5 | 10 | 50 | 100 | 250 | 500 | 1,000 |
| Methanol (μL) | 367.6 | 337.6 | 300 | 365.6 | 356.2 | 328.0 | 281.2 | 187.6 |
| STD (μL) @ 2,000 ng/mL | — | — | — | 9.3 | 18.8 | 46.9 | 93.8 | 187.5 |
| Diluted STD (μL) @ 50 ng/mL | 7.5 | 37.5 | 75.0 | — | — | — | — | — |

The calibration curve for analytes was prepared with 90 μL of stock internal standard solution, 1.5 mL of synthetic negative saliva, and the specific components listed in Table 5. After the set of concentrations were prepared, they were vortexed for 10 seconds to ensure proper mixing of standard and internal standard solutions.

The calibration curve for alcohol is listed in Table 6. After the set of concentrations were prepared, they were vortexed for 10 seconds to ensure proper mixing of standard and internal standard solutions.

Results and Discussion

Sample Collection of Oral Fluid

From both the sublingual and submandibular sites where oral fluid was collected, the collection pad absorbed approximately 1 mL of oral fluid (±10%) within 2 to 5 minutes. Oral fluid is excreted primarily by three glands: the parotid, submaxillary and sublingual glands, as well as by other smaller glands in the head region. Oral fluid is a composite tissue comprised primarily of saliva, buccal and mucosal transudates, gingival crevicular fluid, cellular debris, bacteria, and residues of ingested products. Drug concentrations in oral fluid generally are related to concentrations in blood, but also may be present as residual drug in the oral cavity. The buccal cavity contains mucous membranes that provide a depot effect which allows absorption of higher concentrations of certain drugs such as cocaine and amphetamines. This local absorption effect is due to the higher fat solubility and ease of penetration through membranes with low partitioning from blood to oral fluid.

Oral Fluid Duration from Collection to Report Generation Compared to Lab X

Table 7 shows the number of days from collection of samples to the reporting of the test results for our laboratory for each of the twenty post-mortem subjects compared to Lab X. The average number of days from collection to reporting for our laboratory ranged from 1 to 18 days, with an average of 5.7 days, compared to a range from 7 to 29 days, with an average of 16.4 days for Lab X. Thus, our laboratory was able to collect and report out both qualitative and quantitative results using the methods of the present invention at least two times faster than Lab X.

TABLE 7

Number of Days from Sample Collection to Report Generation

| Decedent ID | Our Laboratory | Lab X |
|---|---|---|
| PM-1 | 5 | 13 |
| PM-2 | 5 | 17 |
| PM-3 | 2 | 16 |
| PM-4 | 2 | 18 |
| PM-5 | 6 | 9 |
| PM-6 | 4 | 15 |
| PM-7 | 4 | 7 |
| PM-8 | 4 | 11 |
| PM-9 | 4 | 18 |
| PM-10 | 4 | 13 |
| PM-11 | 4 | 16 |
| PM-12 | 4 | 16 |
| PM-13 | 4 | 27 |
| PM-14 | 18 | 29 |
| PM-15 | 18 | 21 |
| PM-16 | 1 | 14 |
| PM-17 | 4 | 13 |
| PM-18 | 1 | 17 |
| PM-19 | 3 | 14 |
| PM-20* | 16 | 7 |

*PM-20 is an outlier because a new column needed to be delivered from the manufacturer.

Our validated method utilized accounts for a 1:4 dilution (oral fluid:total parts). A calibration curve and multiple sets of QC were included in every analysis. Upon completion of the run, the calibrator concentrations were analyzed using Agilent MassHunter Quantitative Analysis. The calibration curve was analyzed for linearity to ensure the accuracy of the data. The linearity coefficient ($R^2$) was greater than 0.997 for each analyte of interest. The curve was analyzed for outliers and abundance of signal. QC was verified to ensure the instrumentation and technique of sample preparation was adequate.

Provided below are the test results from the twenty sets of post-mortem samples analyzed both qualitatively and quantitatively using oral fluid as the matrix for drug testing in the fifteen post-mortem subjects, compared to the matrices collected and analyzed by Lab X, shown in Table 8.

TABLE 8

Sample Matrices Analyzed by Lab X for PM 1-20

| | |
|---|---|
| [a]1 | Peripheral Blood |
| [b]2 | Urine |
| [c]3 | Hospital Blood |
| [d]4 | Blood |
| [e]5 | Bile |
| [f]6 | Liver Tissue* |

*Concentrations measured in ng/g.
"Peripheral," "Hospital" and "Blood" are all referred to herein as "Blood."

Post-Mortem Subject 1
Qualitative Analysis

As shown in Table 9, the post-mortem sample collection of oral fluid from the indicated sites in accordance with the invention detected two drugs. Lab X detected the same two drugs and methadone collected from blood.

TABLE 9

ELISA Results for PM-01

| Presumptive Positive in Oral Fluid | Lab X Presumptive Positive |
|---|---|
| Benzodiazepines (SL, SM) | [b]Benzodiazepines |
| Not Reported | [b]Methadone |
| Opiates (SL, SM) | [b]Opiates |

Quantitative Analysis

As shown in FIG. 1, the analysis of oral fluid yielded concentrations of 6-acetylmorphine and morphine which were greater than, and concentrations of alprazolam, codeine, and morphine which were substantially similar to, the concentrations of the same drugs in this subject taken from blood reported by Lab X. In addition, we were able to quantify the concentration of methadone in oral fluid, whereas Lab X could not.

Post-Mortem Subject 2
Qualitative Analysis

As shown in Table 10, the post-mortem sample collection of oral fluid from the indicated sites in accordance with the invention detected three drugs. Lab X's results collected from blood showed the presence of two of the three drugs.

TABLE 10

ELISA Results for PM-2

| Presumptive Positive | Lab X Presumptive Positive |
|---|---|
| Benzodiazepines (SL, SM) | [b]Benzodiazepines |
| Carisoprodol (SL, SM) | Not Reported |
| Oxycodone (SL, SM) | [b]Oxycodone |

Quantitative Analysis

Figure 2:
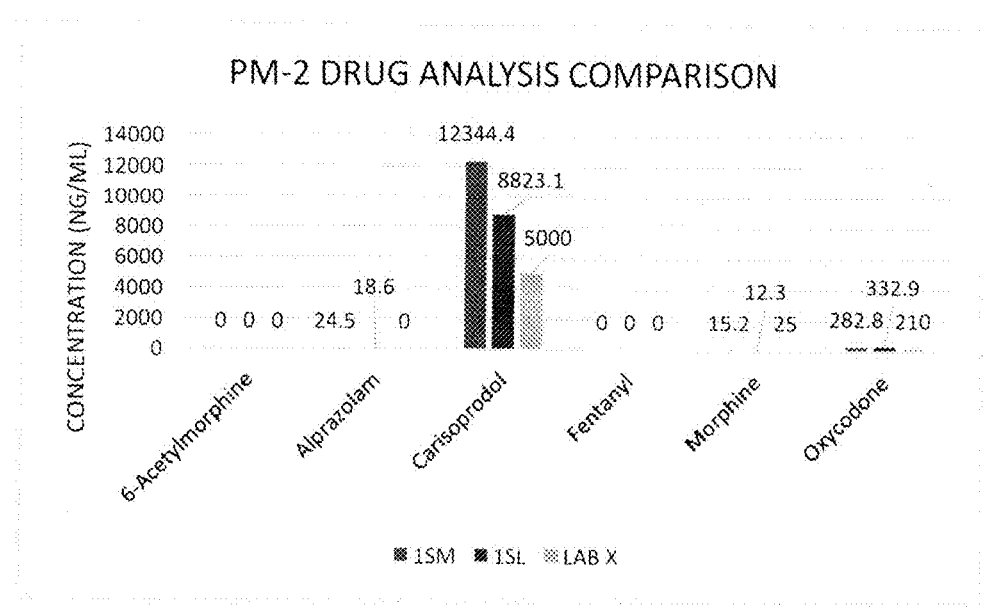
FIG. 2 is a bar graph showing concentrations of 6-acetylmorphine, alprazolam, carisoprodol, fentanyl, morphine, and oxycodone collected from oral fluid of a post-mortem subject (PM-2) in accordance with an embodiment of the invention, compared to concentrations of the same drugs detected in blood from this subject reported by Lab X.

As shown in FIG. 2, the analysis of oral fluid yielded concentrations of carisoprodol which were greater than, and concentrations of morphine and oxycodone which were substantially similar to the concentrations of the same drugs in this subject taken from blood reported by Lab X. In addition, we were able to quantify the concentration of alprazolam in oral fluid, whereas Lab X could not.

Post-Mortem Subject 3
Qualitative Analysis

As shown in Table 11, the post-mortem sample collection of oral fluid in accordance with the invention detected five drugs. Lab X's results collected from blood did not detect any drugs.

TABLE 11

ELISA Results for PM-3

| Presumptive Positive | Lab X Presumptive Positive |
|---|---|
| Cannabinoids (SL, SM) | Not Reported |
| Carisoprodol (SL, SM) | Not Reported |
| Cocaine/Benzoylecgonine (SL, SM) | Not Reported |
| Fentanyl (SL, SM) | Not Reported |
| Opiates (SL, SM) | Not Reported |

Quantitative Analysis

Figure 3:
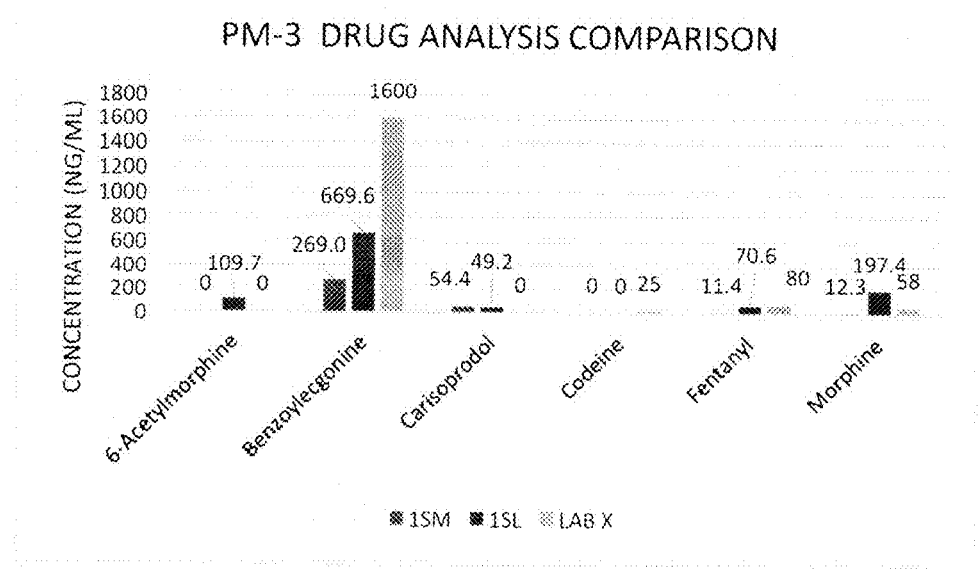
FIG. 3 is a bar graph showing concentrations of 6-acetylmorphine, benzoylecgonine, carisoprodol, codeine, fentanyl, and morphine collected from oral fluid of a post-mortem subject (PM-3) in accordance with an embodiment of the invention, compared to concentrations of the same drugs detected in blood from this subject reported by Lab X.

As shown in FIG. 3, the analysis of oral fluid yielded concentrations of morphine that was greater than, and concentrations of fentanyl which were substantially similar to concentrations of the same drugs in this subject taken from peripheral blood reported by Lab X, except for benzoylecgonine which was greater for Lab X. In addition, we were able to quantify the concentration of 6-acetylmorphine and carisoprodol in oral fluid, whereas Lab X could not. Lab X also was able to quantify the concentration of codeine in this sample.

Post-Mortem Subject 4

Qualitative Analysis

As shown in Table 12, the post-mortem sample collection of oral fluid in accordance with the invention detected four drugs. Lab X's results collected from blood did not detect any drugs.

TABLE 12

ELISA Results for PM-04

| Presumptive Positive | Lab X Presumptive Positive |
|---|---|
| Benzodiazepines (SM) | Not Reported |
| Meperidine (SM) | Not Reported |
| Opiates (SL, SM) | Not Reported |
| Oxycodone (SL) | Not Reported |

Quantitative Analysis

Figure 4:
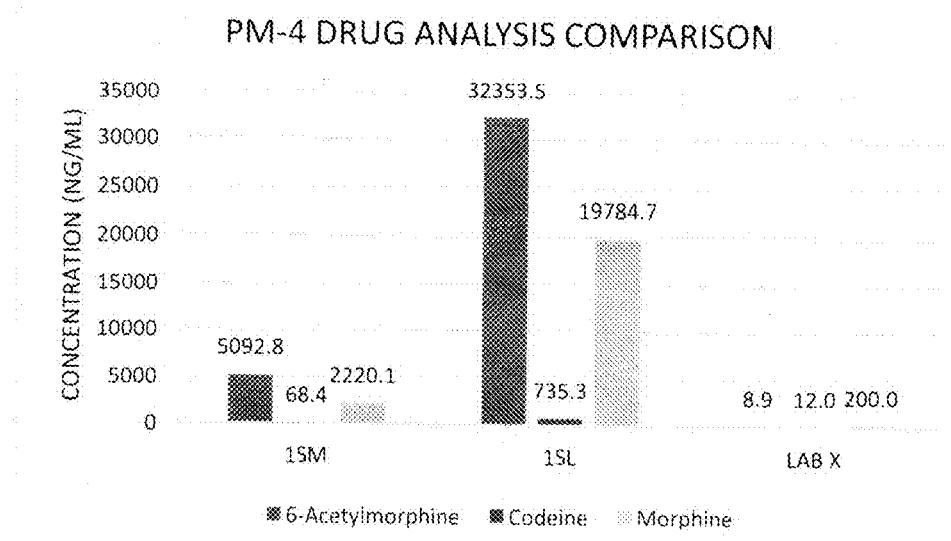
FIG. 4 is a bar graph showing concentrations of 6-acetylmorphine, codeine, and morphine collected from oral fluid of a post-mortem subject (PM-4) in accordance with an embodiment of the invention, compared to concentrations of the same drugs detected in blood from this subject reported by Lab X.

As shown in FIG. 4, the analysis of oral fluid yielded concentrations of 6-acetylmorphine, codeine, and morphine which were greater than the concentrations of these drugs in this subject taken from blood reported by Lab X.

Post-Mortem Subject 5

Qualitative Analysis

As shown in Table 13, the post-mortem sample collection of oral fluid in accordance with the invention detected three drugs. Lab X's results collected from peripheral blood did not detect any drugs.

TABLE 13

ELISA Results for PM-5

| Presumptive Positive | Lab X Presumptive Positive |
|---|---|
| Benzodiazepines (SL, SM) | Not Reported |
| Cannabinoids (SL, SM) | Not Reported |
| Fentanyl (SL, SM) | Not Reported |

Quantitative Analysis

Figure 5:
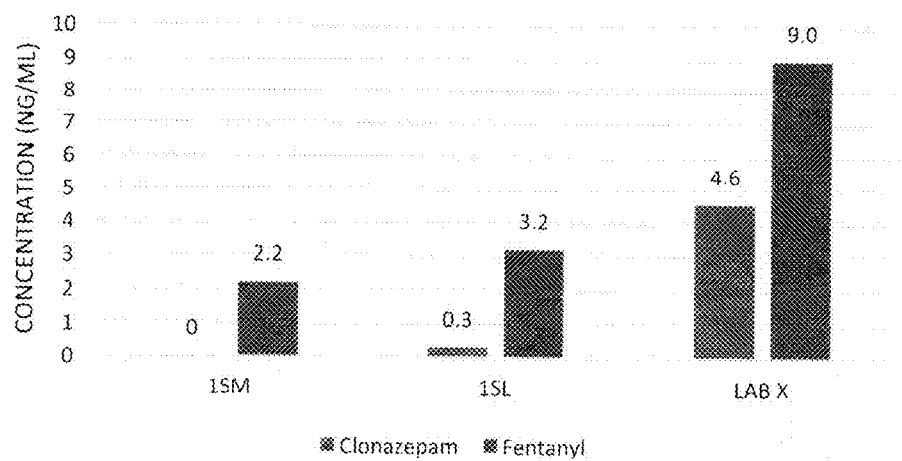
FIG. 5 is a bar graph showing concentrations of clonazepam and fentanyl collected from oral fluid of a post-mortem subject (PM-5) in accordance with an embodiment of the invention, compared to concentrations of the same drugs detected in blood from this subject reported by Lab X.

As shown in FIG. 5, the analysis of oral fluid yielded concentrations of clonazepam and fentanyl which were substantially similar to the concentrations of these drugs in this subject taken from blood reported by Lab X.

Post-Mortem Subject 6

Qualitative Analysis

As shown in Table 14, the post-mortem sample collection of oral fluid in accordance with the invention detected four drugs. Lab X's results collected from blood showed the presence of two of the four drugs.

TABLE 14

ELISA Results for PM-6

| Presumptive Positive | Lab X Presumptive Positive |
|---|---|
| Amphetamine (SL) | Not Reported |
| Cannabinoids (SL, SM) | $^b$Cannabinoids |
| Fentanyl (SL, SM) | Not Reported |
| Opiates (SL) | $^b$Opiates |

Quantitative Analysis

Figure 6:
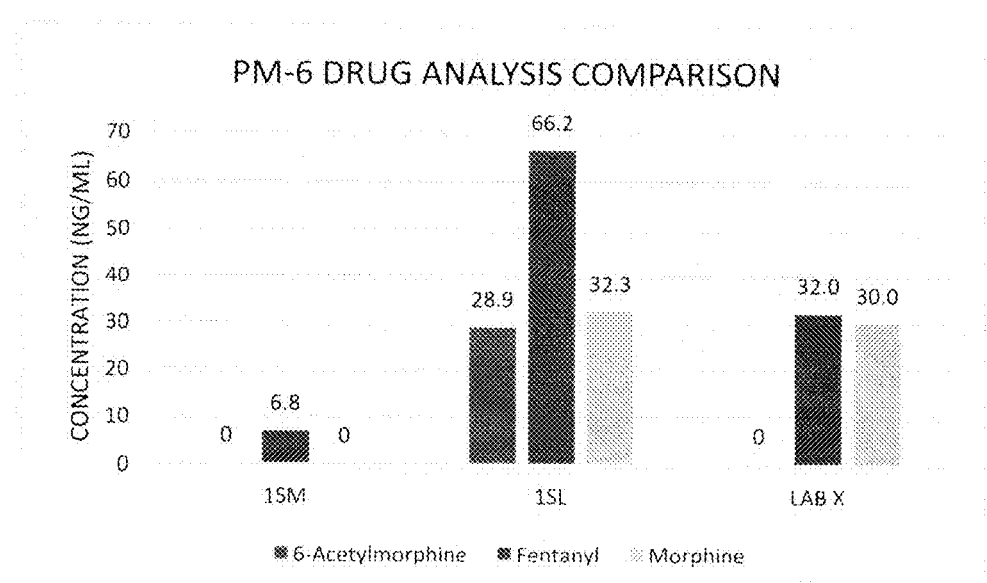
FIG. 6 is a bar graph showing concentrations of 6-acetylmorphine, fentanyl, and morphine collected from oral fluid of a post-mortem subject (PM-6) in accordance with an embodiment of the invention, compared to concentrations of the same drugs detected in blood from this subject reported by Lab X.

As shown in FIG. 6, the analysis of oral fluid yielded concentrations of fentanyl which were greater than, and concentrations of morphine which was substantially similar to concentrations of the same drugs in this subject taken from peripheral blood reported by Lab X. In addition, we were able to quantify the concentration of 6-acetylmorphine in oral fluid, whereas Lab X could not.

Post-Mortem Subject 7

Qualitative Analysis

As shown in Table 15, the post-mortem sample collection of oral fluid in accordance with the invention detected one drug. Lab X's results collected from blood did not detect any drugs.

TABLE 15

ELISA Results for PM-7

| Presumptive Positive | Lab X Presumptive Positive |
|---|---|
| Fentanyl (SL, SM) | Not Reported |

Quantitative Analysis

Figure 7:
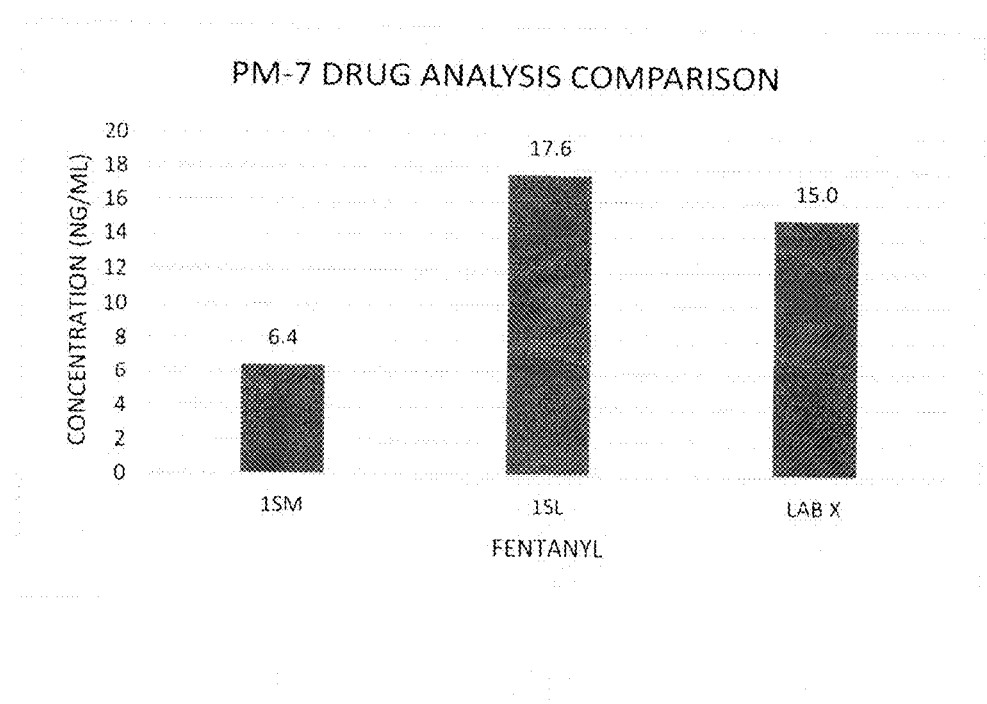
FIG. 7 is a bar graph showing the concentration of fentanyl collected from oral fluid of a post-mortem subject (PM-7) in accordance with an embodiment of the invention compared to the concentration of the same drug detected in blood from this subject reported by Lab X.

As shown in FIG. 7, the analysis of oral fluid yielded a concentration of fentanyl which was substantially similar to the concentration of this drug taken from blood reported by Lab X.

Post-Mortem Subject 8

Qualitative Analysis

As shown in Table 16, the post-mortem sample collection of oral fluid in accordance with the invention detected four drugs. Lab X's results collected from blood detected three of these drugs, as well as oxycodone.

TABLE 16

ELISA Results for PM-8

| Presumptive Positive | Lab X Presumptive Positive |
|---|---|
| Amphetamine (SL) | Not Reported |
| Cannabinoids (SL, SM) | $^b$Cannabinoids |
| Benzodiazepines (SL, SM) | $^b$Benzodiazepines |
| Opiates (SL) | $^b$Opiates |
| Not Reported | $^b$Oxycodone |

Quantitative Analysis

Figure 8:
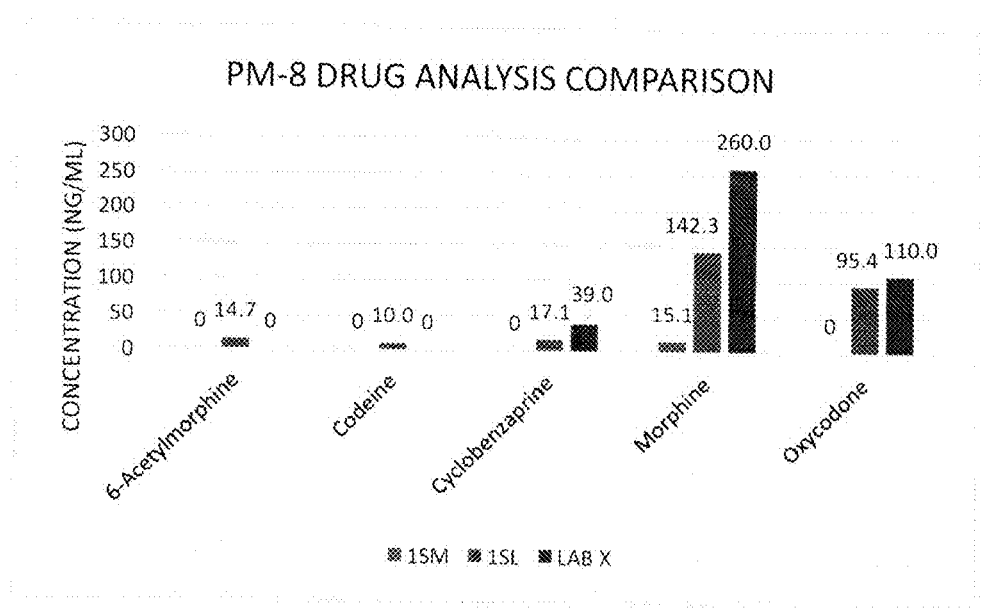
FIG. 8 is a bar graph showing concentrations of 6-acetylmorphine, codeine, cyclobenzaprine, morphine, and oxycodone collected from oral fluid of a post-mortem subject (PM-8) in accordance with an embodiment of the invention, compared to concentrations of the same drugs detected in blood from this subject reported by Lab X.

As shown in FIG. 8, the analysis of oral fluid yielded concentrations of 6-acetylmorphine and codeine which were not able to be quantified in this subject taken from peripheral blood reported by Lab X. The concentration of oxycodone was substantially similar to concentrations of this drug reported by Lab X. Concentrations of cyclobenzaprine and morphine were greater from Lab X.

Post-Mortem Subject 9

Qualitative Analysis

As shown in Table 17, the post-mortem sample collection of oral fluid in accordance with the invention detected five drugs. Lab X's results collected from blood showed the detection of only one of these drugs.

TABLE 17

ELISA Results for PM-9

| Presumptive Positive | Lab X Presumptive Positive |
|---|---|
| Amphetamine (SL) | Not Reported |
| Benzodiazepines (SL, SM) | Not Reported |
| Cocaine/Benzoylecgonine (SL) | Not Reported |
| Methadone (SL, SM) | $^b$Methadone |
| Opiates (SL) | Not Reported |

Quantitative Analysis

Figure 9:
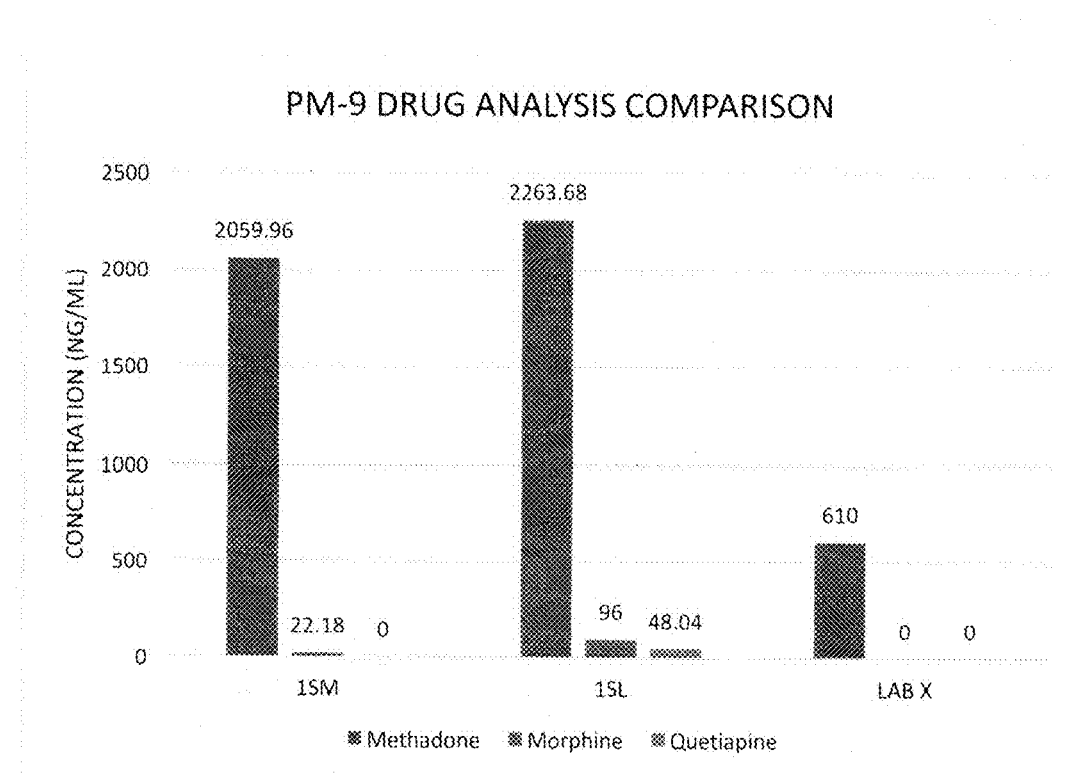
FIG. 9 is a bar graph showing concentrations of methadone, morphine and quetiapine collected from oral fluid of a post-mortem subject (PM-9) in accordance with an embodiment of the invention, compared to concentrations of the same drugs detected in blood from this subject reported by Lab X.

As shown in FIG. 9, the analysis of oral fluid yielded a concentration of methadone which was greater than the concentration of this drug in this subject taken from blood reported by Lab X. In addition, we were able to quantify the concentrations of morphine and quetiapine in oral fluid, whereas Lab X could not.

Post-Mortem Subject 10

Qualitative Analysis

As shown in Table 18, the post-mortem sample collection of oral fluid in accordance with the invention detected three drugs. Lab X's results collected from blood detected one of these drugs, as well as opiates and oxycodone.

TABLE 18

ELISA Results for PM-10

| Presumptive Positive | Lab X Presumptive Positive |
|---|---|
| Amphetamine (SL) | Not Reported |
| Cannabinoids (SL, SM) | [b]Cannabinoids |
| Methadone (SL) | Not Reported |
| Not Reported | Not Reported |
| Not Reported | [b]Opiates |
| Not Reported | [b]Oxycodone |

Quantitative Analysis

Figure 10:
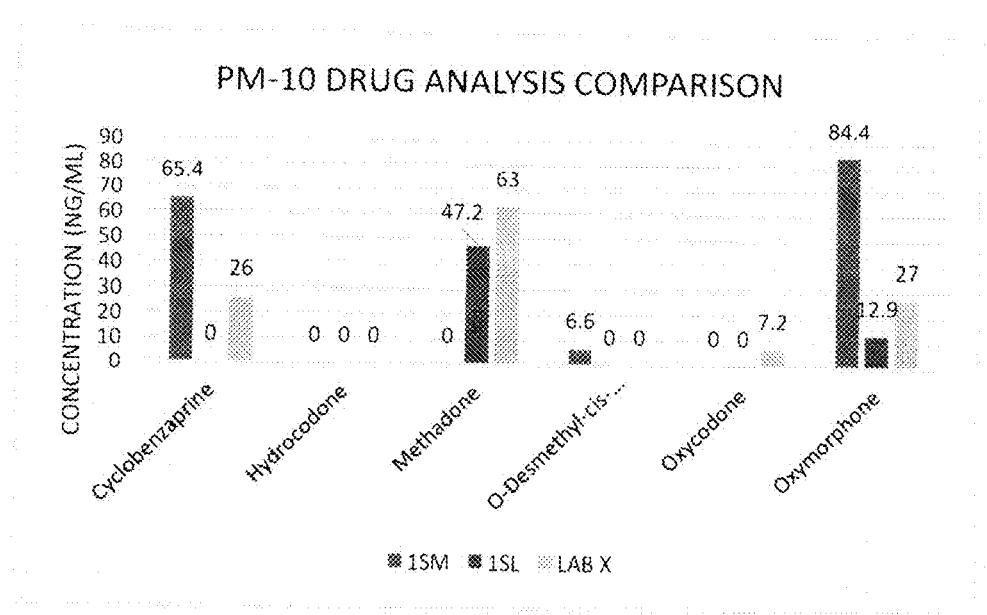
FIG. 10 is a bar graph showing concentrations of cyclobenzaprine, hydrocodone, methadone, o-desmethyl-cis-tramadol, oxycodone, and oxymorphone collected from oral fluid of a post-mortem subject (PM-10) in accordance with an embodiment of the invention, compared to concentrations of the same drugs detected in blood from this subject reported by Lab X.

As shown in FIG. 10, the analysis of oral fluid yielded concentrations of cyclobenzaprine and oxymorphone which was greater than, and a concentration of methadone which was substantially similar to, concentrations of these drugs in this subject taken from blood reported by Lab X. In addition, we were able to quantify the concentration of o-desmethyl-cis-tramadol in oral fluid, whereas Lab X could not. Lab X was able to quantify the concentration of oxycodone, where we did not.

Post-Mortem Subject 11

Qualitative Analysis

As shown in Table 19, the post-mortem sample collection of oral fluid in accordance with the invention detected four drugs. Lab X's results collected from blood detected two of the four drugs.

TABLE 19

ELISA Results for PM-11

| Presumptive Positive | Lab X Presumptive Positive |
|---|---|
| Amphetamine (SL) | Not Reported |
| Cocaine/Benzoylecgonine (SL, SM) | [b]Cocaine/Metabolites |
| Fentanyl (SL, SM) | Not Reported |
| Opiates (SL) | [b]Opiates |

Quantitative Analysis

Figure 11:
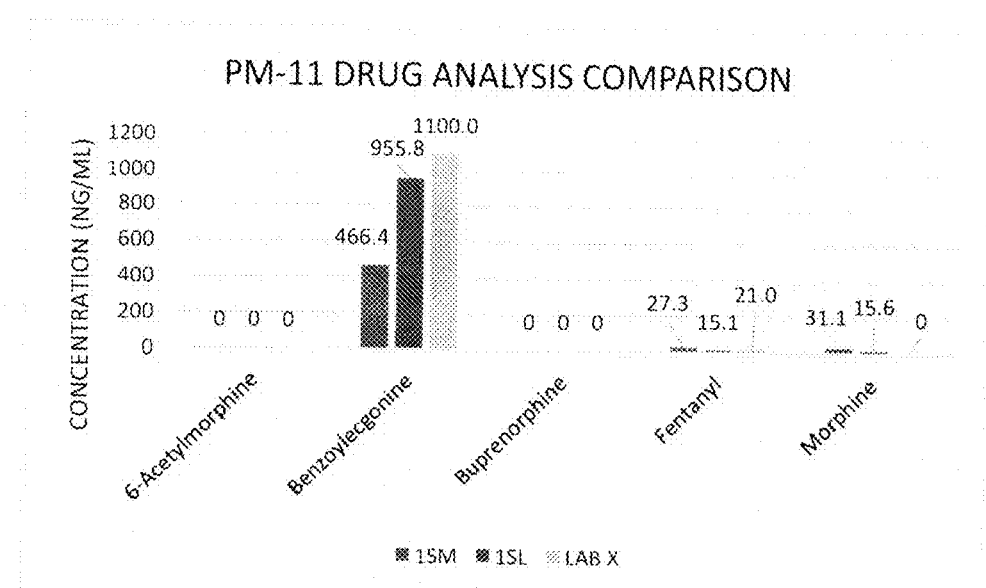
FIG. 11 is a bar graph showing concentrations of 6-acetylmorphine, benzoylecgonine, buprenorphine, fentanyl, and morphine collected from oral fluid of a post-mortem subject (PM-11) in accordance with an embodiment of the invention, compared to concentrations of the same drugs detected in blood from this subject reported by Lab X.

As shown in FIG. 11, the analysis of oral fluid yielded concentrations of benzoylecgonine and fentanyl which were substantially similar to the concentrations of these drugs in this subject taken from blood reported by Lab X. In addition, we were able to quantify the concentration of morphine in oral fluid, whereas Lab X could not.

Post-Mortem Subject 12

Qualitative Analysis

As shown in Table 20, the post-mortem sample collection of oral fluid in accordance with the invention detected four drugs. Lab X's results collected from blood did not detect any drugs.

TABLE 20

ELISA Results for PM-12

| Presumptive Positive | Lab X Presumptive Positive |
|---|---|
| Amphetamine (SL) | Not Reported |
| Cannabinoids (SL, SM) | Not Reported |
| Fentanyl (SL, SM) | Not Reported |
| Opiates (SL) | Not Reported |

Quantitative Analysis

Figure 12:
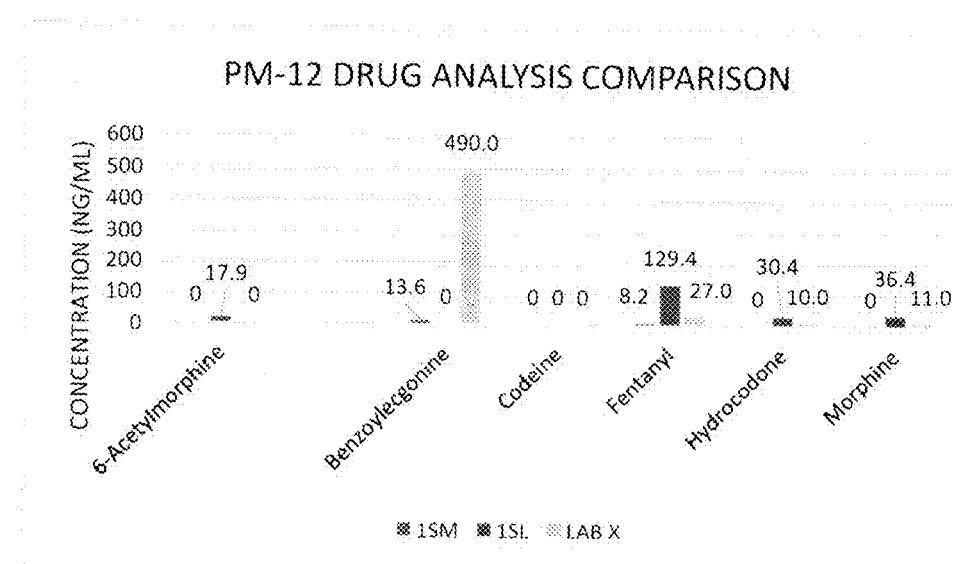
FIG. 12 is a bar graph showing concentrations of 6-acetylmorphine, benzoylecgonine, codeine, fentanyl, hydrocodone, and morphine collected from oral fluid of a post-mortem subject (PM-12) in accordance with an embodiment of the invention, compared to concentrations of the same drugs detected in blood from this subject reported by Lab X.

As shown in FIG. 12, the analysis of oral fluid yielded concentrations of fentanyl, hydrocodone, and morphine which were greater than the concentrations of these drugs in this subject taken from blood reported by Lab X. In addition, we were able to quantify the concentration of 6-acetylmorphine in oral fluid, whereas Lab X could not. Benzoylecgonine was detected in smaller concentrations in oral fluids than was found by Lab X.

Post-Mortem Subject 13

Qualitative Analysis

As shown in Table 21, the post-mortem sample collection of oral fluid in accordance with the invention detected five drugs. Lab X's results collected from blood did not detect any drugs.

TABLE 21

ELISA Results for PM-13

| Presumptive Positive | Lab X Presumptive Positive |
|---|---|
| Amphetamine (SL) | Not Reported |
| Benzodiazepines (SL) | Not Reported |
| Cocaine/Benzoylecgonine (SL) | Not Reported |
| Methamphetamine (SL) | Not Reported |
| Opiates (SL) | Not Reported |

Quantitative Analysis

Figure 13:
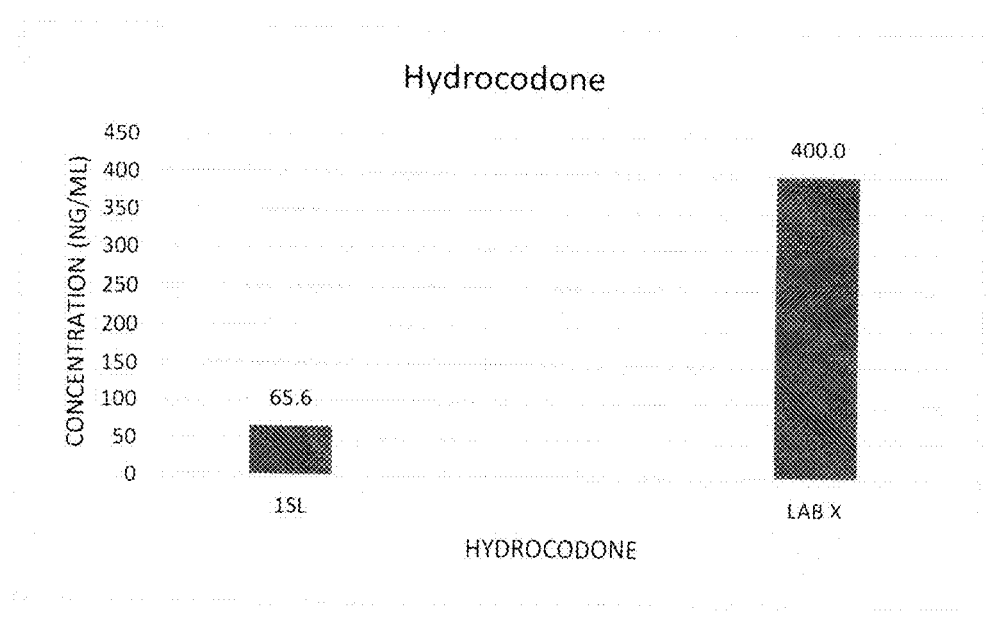
FIG. 13 is a bar graph showing the concentration of hydrocodone collected from oral fluid of a post-mortem subject (PM-13) in accordance with an embodiment of the invention, compared to the concentration of the same drug detected in blood from this subject reported by Lab X.

As shown in FIG. 13, the analysis of oral fluid yielded concentrations of hydrocodone which were less than the concentration of this drug in this subject taken from bile reported by Lab X. It should be noted that this decedent was highly decomposed, and thus Lab X had to determine drug levels in the body through the invasive procedure of extracting bile from the bile duct, which is a difficult and time-consuming process, whereas we were able to determine the concentration of hydrocodone rapidly in oral fluid.

Post-Mortem Subject 14

Qualitative Analysis

As shown in Table 22, the post-mortem sample collection of oral fluid in accordance with the invention detected three drugs. Lab X's results using blood did not detect any drugs.

TABLE 22

ELISA Results for PM-14

| Presumptive Positive | Lab X Presumptive Positive |
|---|---|
| Benzodiazepines (SL) | Not Reported |
| Cocaine/Benzoylecgonine (SL) | Not Reported |
| Fentanyl (SL) | Not Reported |

Quantitative Analysis

Figure 14:
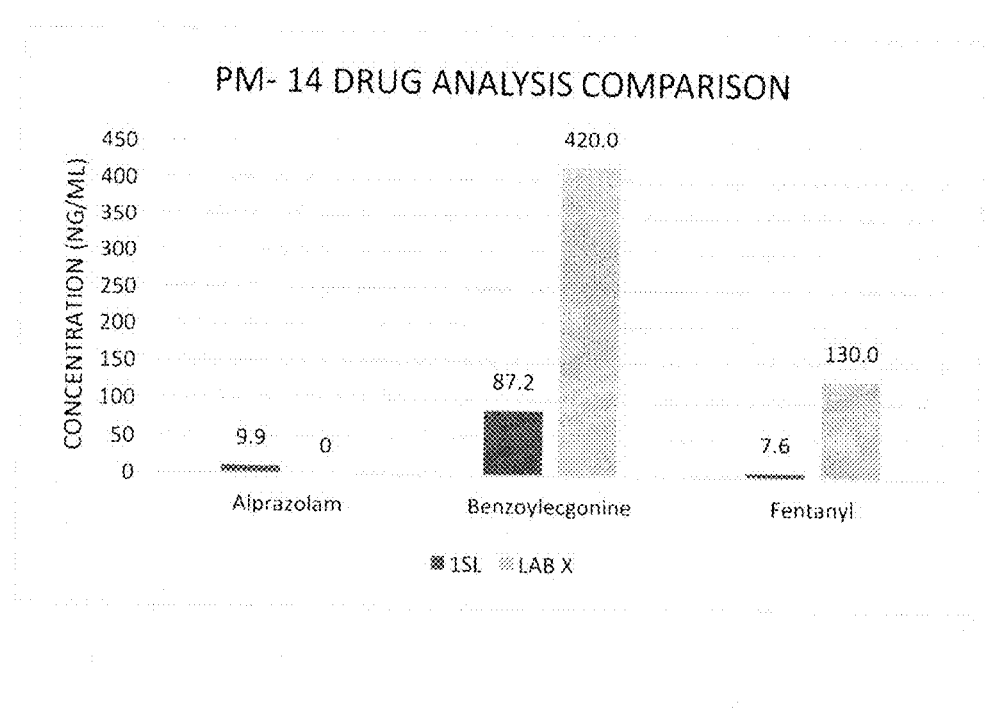
FIG. 14 is a bar graph showing concentrations of alprazolam, benzoylecgonine, and fentanyl collected from oral fluid of a post-mortem subject (PM-14) in accordance with an embodiment of the invention, compared to concentrations of the same drugs detected in blood from this subject reported by Lab X.

As shown in FIG. 14, the analysis of oral fluid yielded a concentration of alprazolam, whereas Lab X was not able to quantify any concentration of this drug. Concentrations of benzoylecgonine and fentanyl were lower in oral fluid than that found in liver tissue in this subject reported by Lab X.

No concentrations of the three drugs were found in blood by Lab X. Again, it should be noted that the concentrations of the two drugs by Lab X were found by using the invasive procedure to extract liver tissue from the decedent, a difficult and time-consuming matrix, compared to our rapid method using oral fluid.

Post-Mortem Subject 15

Qualitative Analysis

As shown in Table 23, the post-mortem sample collection of oral fluid in accordance with the invention detected two drugs. Lab X's results collected from blood detected only one of these drugs.

TABLE 23

ELISA Results for PM-15

| Presumptive Positive | Lab X Presumptive Positive |
|---|---|
| Fentanyl (SL) | Not Reported |
| Opiates (SL) | $^b$Opiates |

Quantitative Analysis

Figure 15:
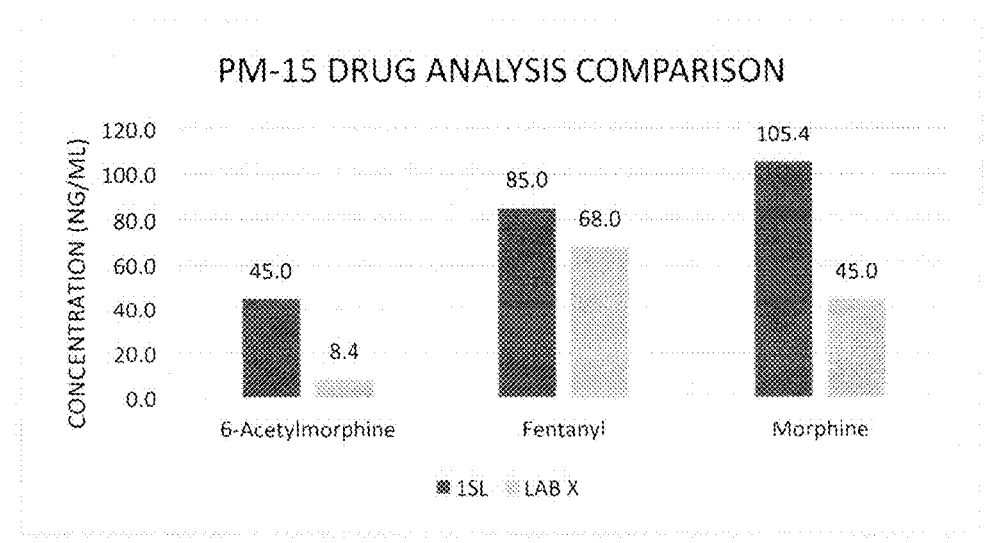
FIG. 15 is a bar graph showing concentrations of 6-acetylmorphine, fentanyl, and morphine collected from oral fluid of a post-mortem subject (PM-15) in accordance with an embodiment of the invention, compared to concentrations of the same drugs detected in blood from this subject reported by Lab X.

As shown in FIG. 15, the analysis of oral fluid yielded concentrations of 6-acetylmorphine, fentanyl, and morphine, in which 6-acetylmorphine and morphine were greater than, and a concentration of fentanyl which was substantially similar to, the concentrations of these drugs in this subject reported by Lab X. Lab X used urine to quantitate 6-acetylmorphine, and blood to quantitate morphine and fentanyl.

The following comments should be noted with respect to the foregoing results reported for the fifteen post-mortem subjects in this study. For PM-3, oral fluid collection from the sublingual site in the buccal cavity yielded low concentrations of codeine (4.63 ng/mL). Because it was below the limit of quantitation, the concentration was estimated and was not reported based upon the validation of the method for codeine. Qualitative analysis, however, showed that codeine was present. This was observed in decedents PM-5 with clonazepam (0.34 ng/mL), PM-10 with cyclobenzaprine and oxycodone (4.74 and 5.53 ng/mL, respectively), and PM-12 for benzoylecgonine (2.41 ng/mL). Benzoylecgonine is the main metabolite of the parent analyte cocaine. Because sublingual samples from the buccal cavity contain large amount of lipids and fatty acids, cocaine is protected from rapid metabolism, thus yielding low concentrations of benzoylecgonine. Additionally, having a more aggressive sample clean up would result in lower cut-off points and thus yield greater concentrations of drug. Additionally, PM-11 and PM-13 were decedents that had a high degree of putrefaction (2 to 10 days, respectively). Thus, PM-13's sample location was collected only from the sublingual site in the buccal cavity. Results showed that analyses completed by both our laboratory and Lab X resulted in similar analytes, except in PM-11 where we detected 6-acetylmorphine and morphine (6.49 and 118.97 ng/mL, respectively). Lab X utilized 6-monoacetylmorphine as its analyte of choice instead of 6-acetylmorphine.

The results reported by our laboratory and Lab X show that benzoylecgonine, codeine, fentanyl, and morphine were common analytes reported by both laboratories. Importantly, the use of oral fluid had a further advantage of being able to detect and report concentrations of two additional analytes: 6-acetylmorphine and carisoprodol, two drugs not reported in blood from Lab X. The ability to screen and quantify these two additional analytes, which has been shown to contribute to the cause of death, can be critical in identifying the exact cause of death in a particular decedent. Another advantage of the use of oral fluid is in cases of post-mortem decomposition, where oral fluid is a superior alternative to blood, bile, and liver tissue, because of the process of autolysis and the difficulty in retrieving samples for analysis from these matrices.

Provided below are test results from five additional post-mortem samples (PM-16, PM-17, PM-18, PM-19 and PM-20) analyzed quantitatively using oral fluid as the matrix for drug testing in the five post-mortem subjects, compared to blood as the matrix collected and analyzed from the same subjects by Lab X. In addition, seven other non-naturally occurring drugs underwent validation testing: zolpidem, nortriptyline, dextromethorphan, zopiclone, zaleplon, MDA and MDEA. All seven of these drugs were validated with respect to the use of the LC-MS/MS method to quantify non-naturally occurring drugs taken from oral fluid from post-mortem subjects.

Figure 16:
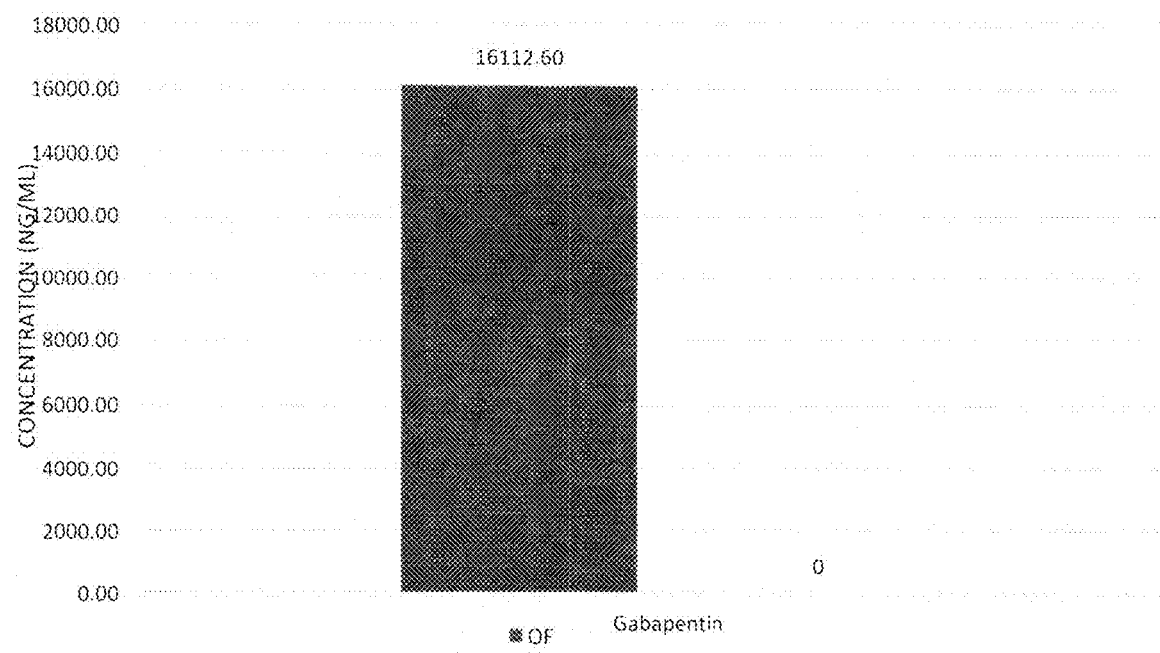
FIG. 16 is a bar graph showing the concentration of gabapentin collected from oral fluid of a post-mortem subject (PM-16) in accordance with an embodiment of the invention, compared to the concentration of the same drug detected in blood from this subject reported by Lab X.

As shown in FIG. 16, we were able to quantify the concentration of gabapentin in oral fluid in this subject, which concentration was extremely high, whereas Lab X could not quantify the concentration of this drug taken from blood in the same subject.

Figure 17:
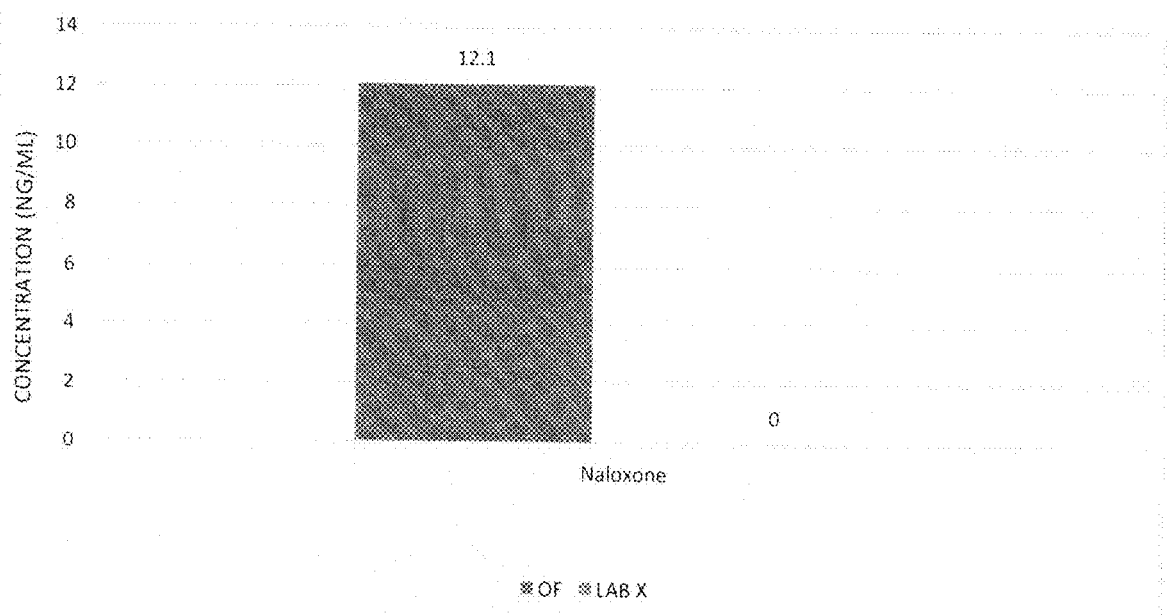
FIG. 17 is a bar graph showing the concentration of naloxone collected from oral fluid of a post-mortem subject (PM-17) in accordance with an embodiment of the invention, compared to the concentration of the same drug detected in blood from this subject reported by Lab X.

As shown in FIG. 17, we were able to quantify the concentration of naloxone in oral fluid in this subject, whereas Lab X could not quantify the concentration of this drug taken from blood in the same subject.

Figure 18:
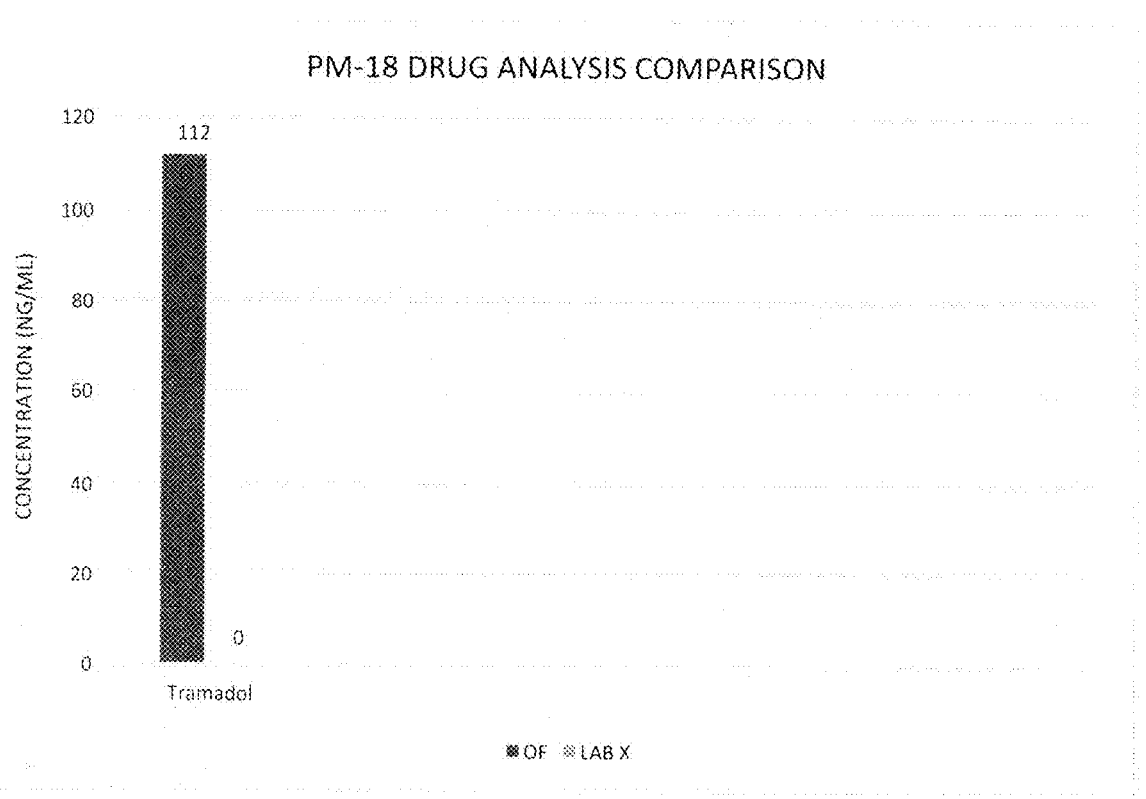
FIG. 18 is a bar graph showing the concentration of tramadol collected from oral fluid of a post-mortem subject (PM-18) in accordance with an embodiment of the invention, compared to the concentration of the same drug detected in blood from this subject reported by Lab X.

As shown in FIG. 18, we were able to quantify the concentration of tramadol in oral fluid in this subject, which concentration was very high, whereas Lab X could not quantify the concentration of this drug taken from blood in the same subject.

Figure 19:
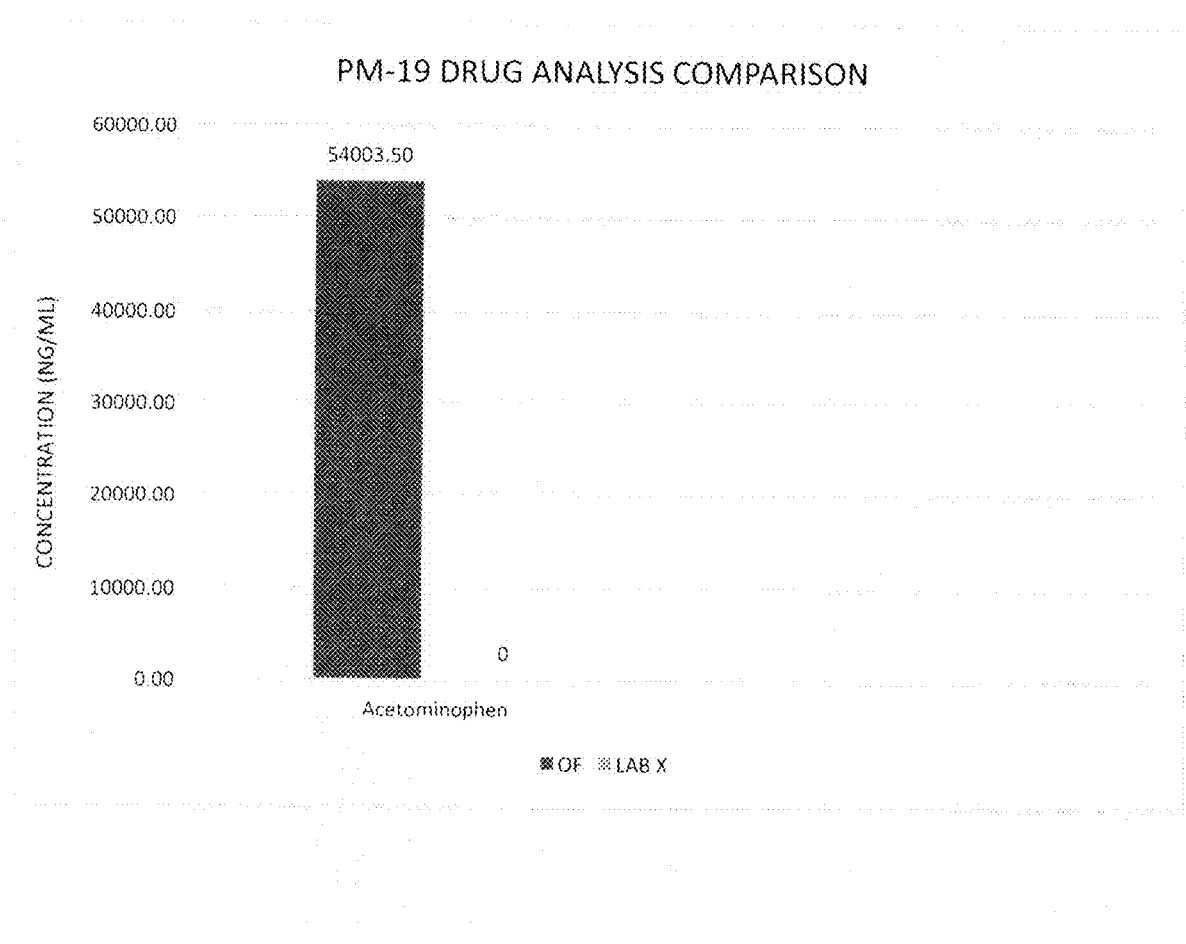
FIG. 19 is a bar graph showing the concentration of acetaminophen collected from oral fluid of a post-mortem subject (PM-19) in accordance with an embodiment of the invention, compared to the concentration of the same drug detected in blood from this subject reported by Lab X.

As shown in FIG. 19, we were able to quantify the concentration of acetaminophen in oral fluid in this subject, which concentration was extremely high, whereas Lab X could not quantify the concentration of this drug taken from blood in the same subject.

Figure 20:
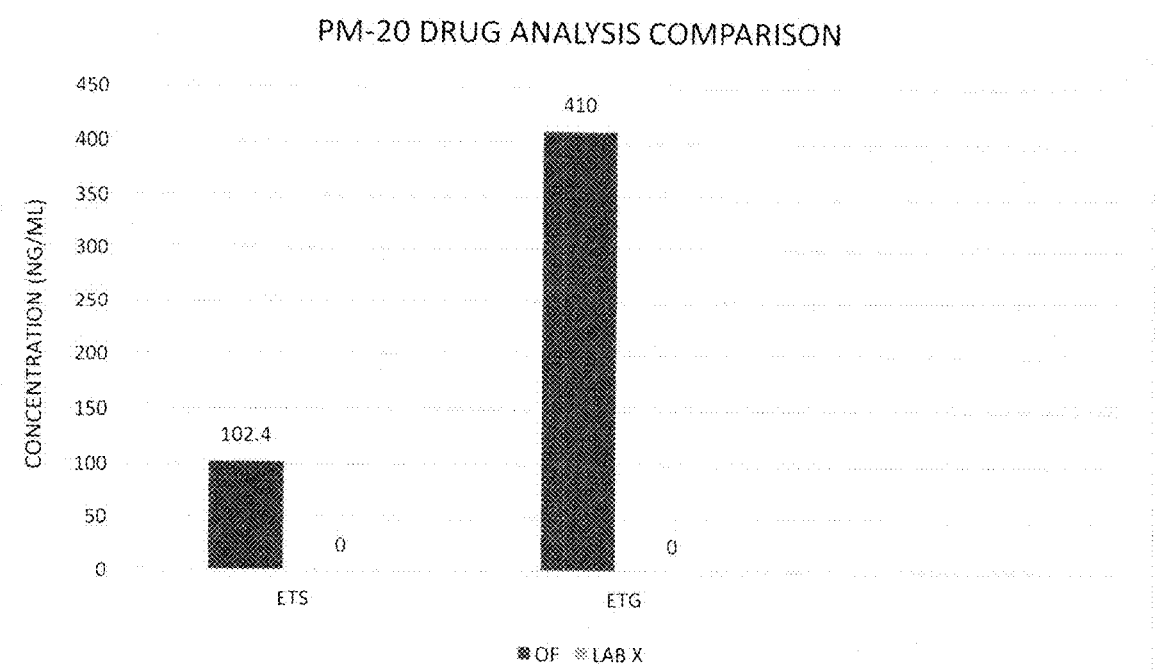
FIG. 20 is a bar graph showing concentrations of the alcohols ethyl sulfate (EtS) and ethyl glucuronide (EtG) collected from oral fluid of a post-mortem subject (PM-20) in accordance with an embodiment of the invention, compared to concentrations of the same drugs detected in blood from this subject reported by Lab X.

As shown in FIG. 20, we were able to quantify the concentrations of EtS and EtG in oral fluid in this subject, whereas Lab X could not quantify the concentrations of these drugs and/or drug metabolites taken from blood in the same subject.

Provided below are test results from six live dogs (SF10085, SF10086, SF10087, SF10088, SF10092, SF10048) and from two post-mortem dogs (SF10093, SF10049) analyzed quantitatively using oral fluid as the matrix for drug testing. The non-naturally occurring drugs which underwent validation testing with respect to the use of the LC-MS/MS method to quantify non-naturally occurring drugs taken from oral fluid from post-mortem subjects were ketamine, methamphetamine, diazepam, acetaminophen, tramadol and gabapentin.

Figure 21:
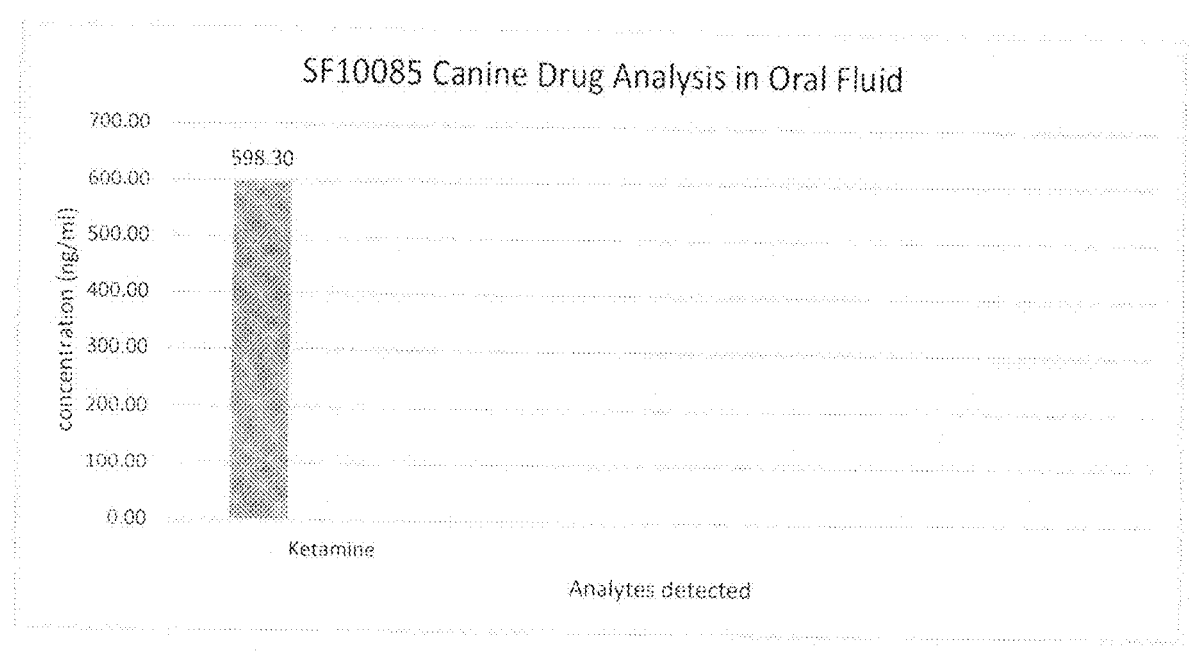
FIG. 21 is a bar graph showing the concentration of ketamine collected from oral fluid of a live dog (SF10085) in accordance with an embodiment of the invention.

As shown in FIG. 21, ketamine was detected and quantified in oral fluid at a concentration of 598.30 ng/mL in a live dog (SF10085).

Figure 22:
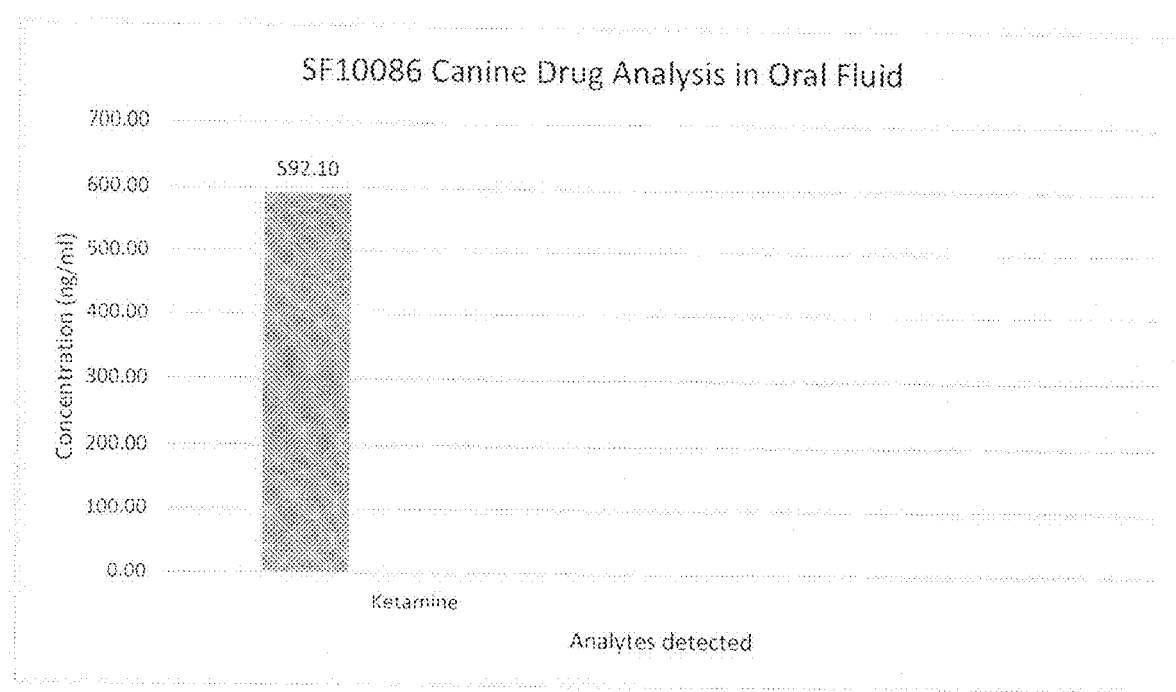
FIG. 22 is a bar graph showing the concentration of ketamine collected from oral fluid of a live dog (SF10086) in accordance with an embodiment of the invention.

As shown in FIG. 22, ketamine was detected and quantified in oral fluid at a concentration of 592.10 ng/mL in a live dog (SF10086).

Figure 23:
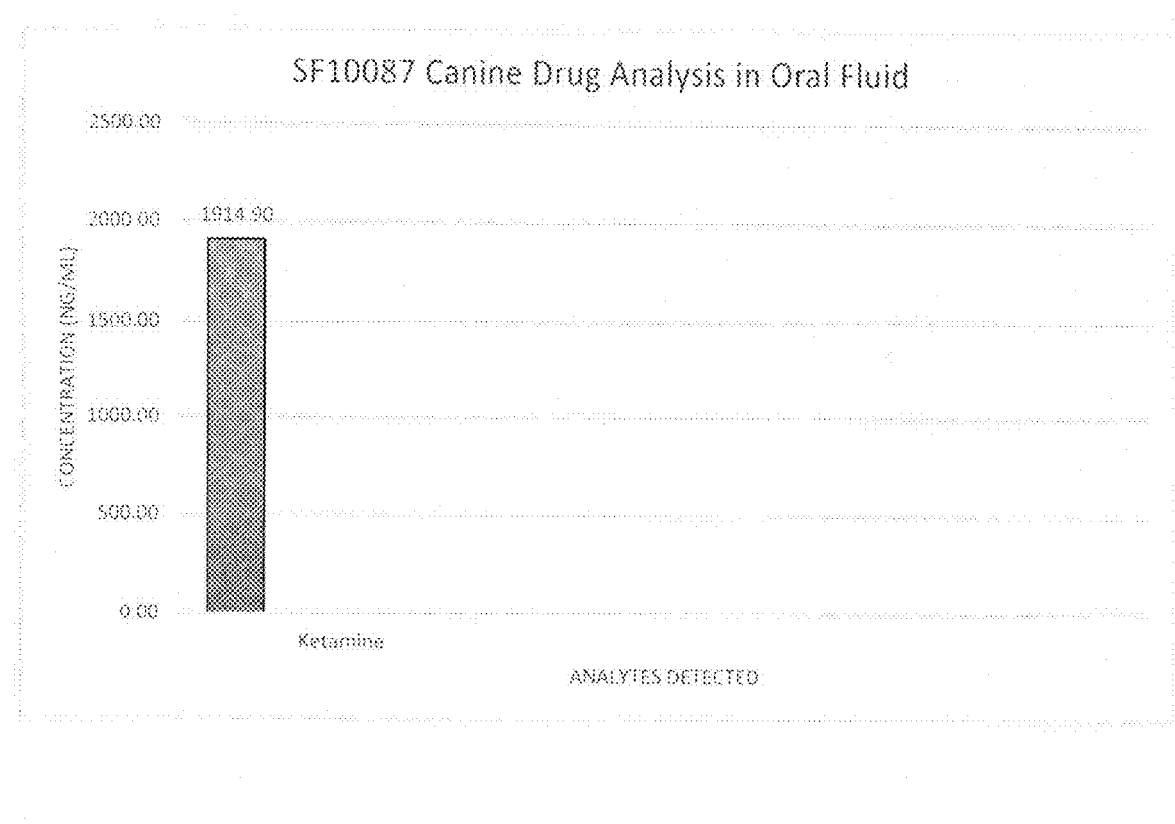
FIG. 23 is a bar graph showing the concentration of ketamine collected from oral fluid of a live dog (SF10087) in accordance with an embodiment of the invention.

As shown in FIG. 23, ketamine was detected and quantified in oral fluid at a concentration of 1914.90 ng/mL in a live dog (SF10087).

Figure 24:
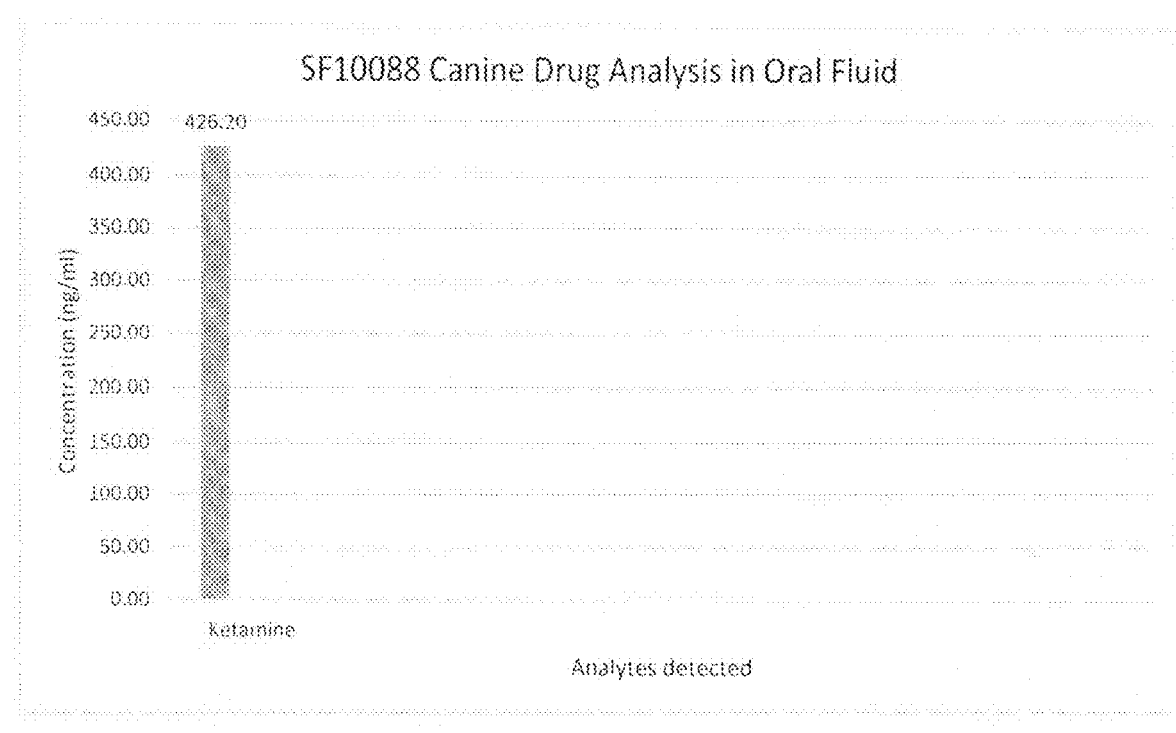
FIG. 24 is a bar graph showing the concentration of ketamine collected from oral fluid of a live dog (SF10088) in accordance with an embodiment of the invention.

As shown in FIG. 24, ketamine was detected and quantified in oral fluid at a concentration of 426.20 ng/mL in a live dog (SF10088).

Figure 25:
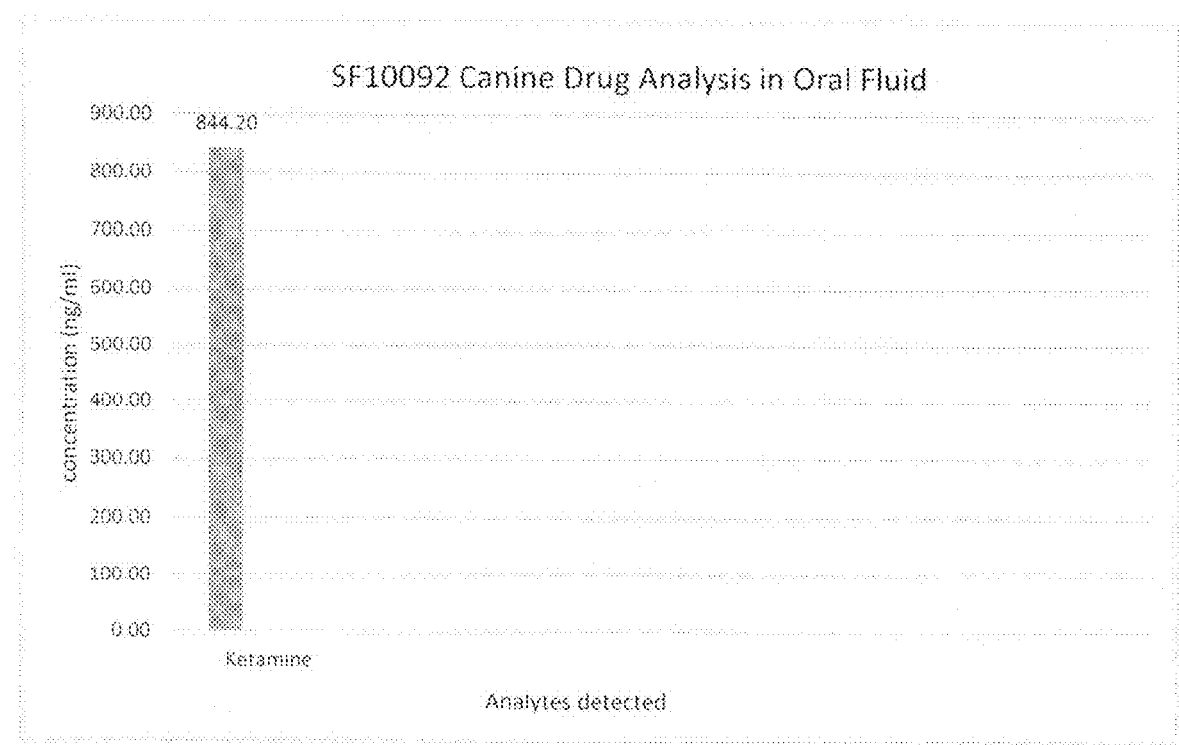
FIG. 25 is a bar graph showing the concentration of ketamine collected from oral fluid of a live dog (SF10092) in accordance with an embodiment of the invention.

As shown in FIG. 25, ketamine was detected and quantified in oral fluid at a concentration of 844.20 ng/mL in a live dog (SF10092).

Figure 26:
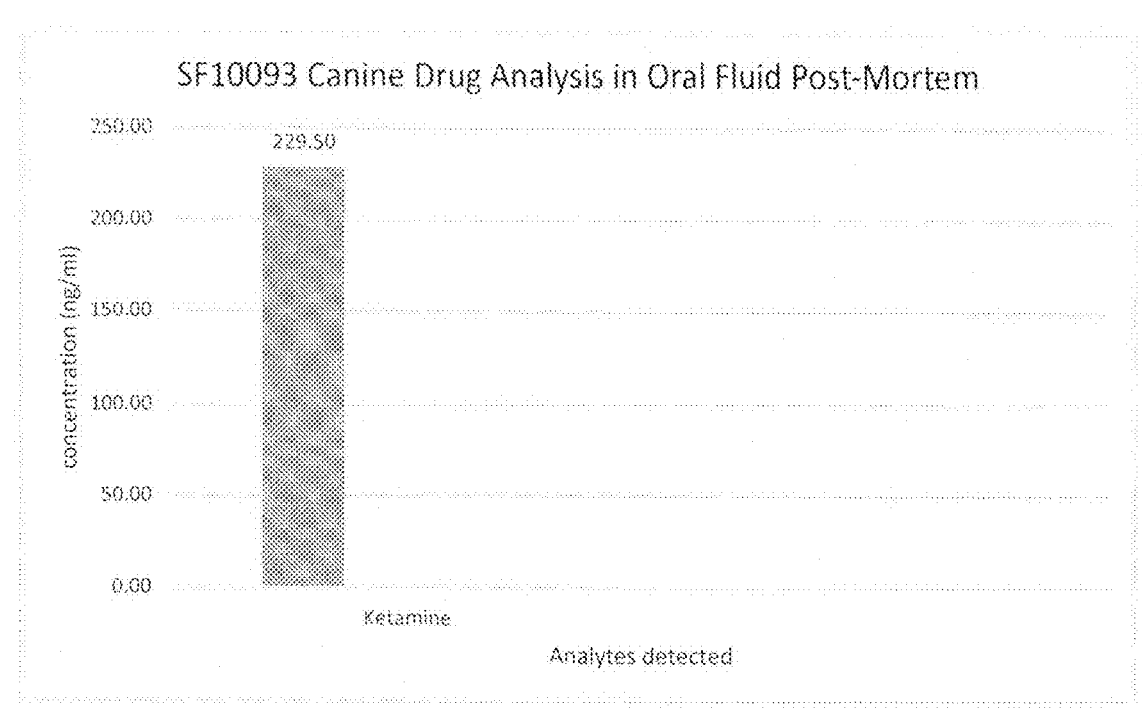
FIG. 26 is a bar graph showing the concentration of ketamine collected from oral fluid of a post-mortem dog (SF10093) in accordance with an embodiment of the invention.

As shown in FIG. 26, ketamine was detected and quantified in oral fluid at a concentration of 229.50 ng/mL in a post-mortem dog (SF10093).

Figure 27:
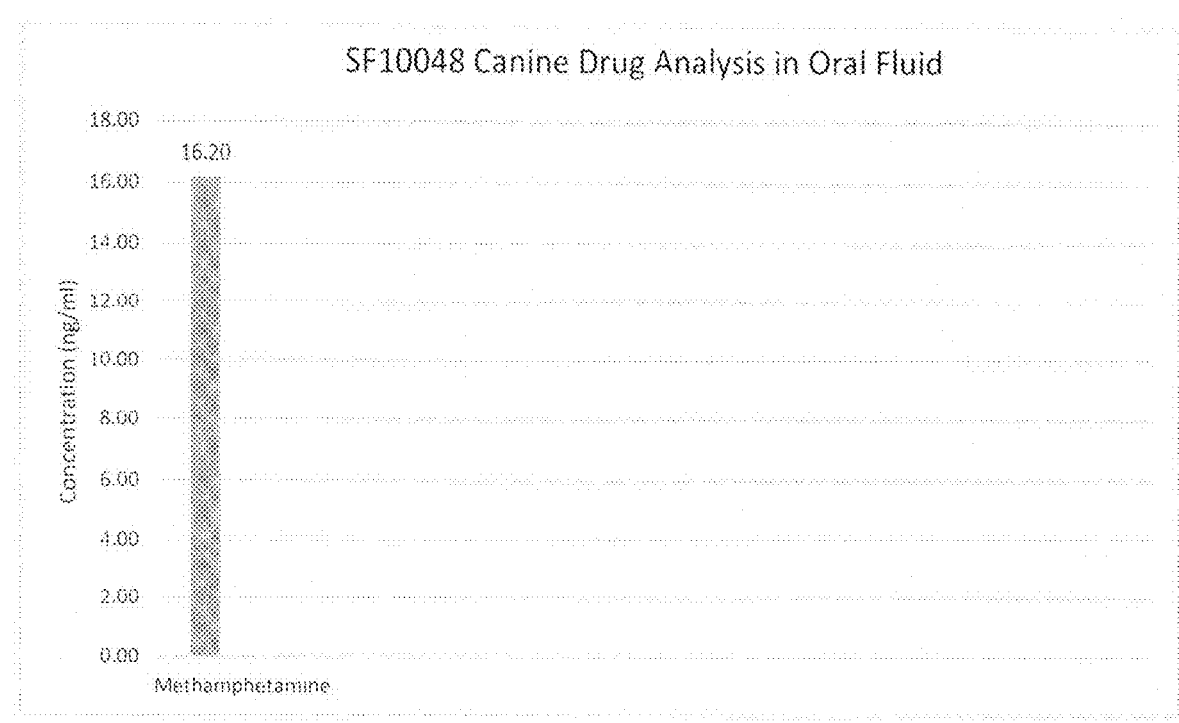
FIG. 27 is a bar graph showing the concentration of methamphetamine collected from oral fluid of a live dog (SF10048) in accordance with an embodiment of the invention.

As shown in FIG. 27, methamphetamine was detected and quantified in oral fluid at a concentration of 16.20 ng/mL in a live dog (SF10048).

Figure 28:
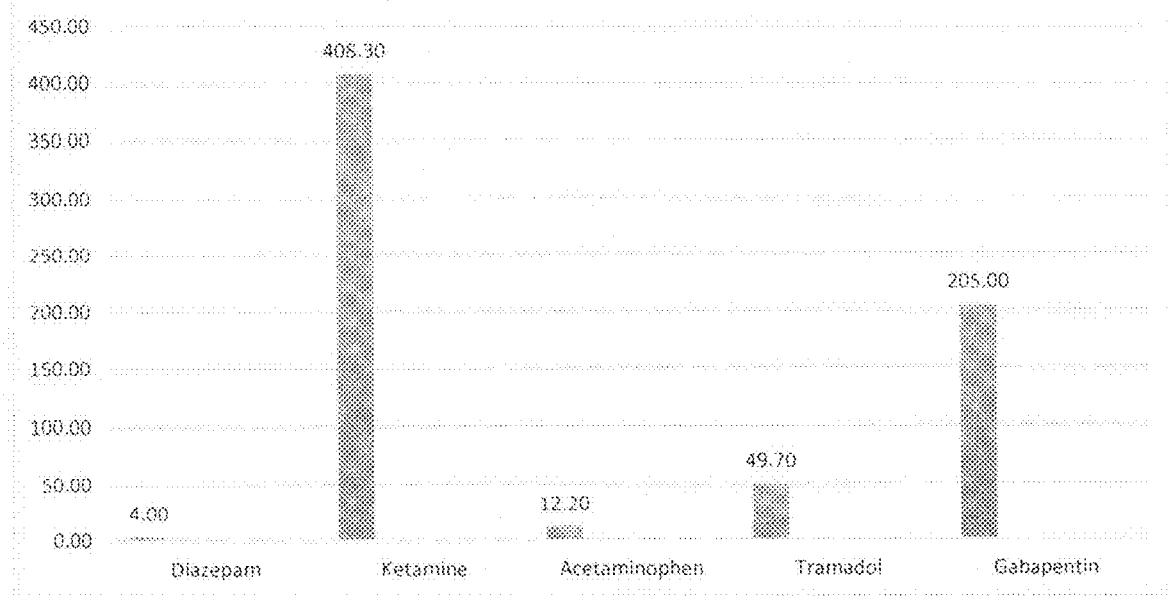
FIG. 28 is a bar graph showing the concentrations of diazepam, ketamine, acetaminophen, tramadol and gabapentin collected from oral fluid of a post-mortem dog (SF10049) in accordance with an embodiment of the invention.

As shown in FIG. 28, in a post-mortem dog (SF10049), diazepam was detected and quantified in oral fluid at a concentration of 4.00 ng/mL, ketamine was detected and quantified in oral fluid at a concentration of 408.30 ng/mL, acetaminophen was detected and quantified in oral fluid at a concentration of 12.20 ng/mL, tramadol was detected and quantified in oral fluid at a concentration of 49.70 ng/mL, and gabapentin was detected and quantified in oral fluid at a concentration of 205.00 ng/mL.

It should be noted that the present invention is not limited to the specific analytes, drugs or drug metabolites disclosed herein, but includes, without limitation, drugs from the following non-limiting drug classes: opioids, benzodiazepines, antidepressants, antihistamines, antipsychotics, anticonvulsants, muscle relaxants, barbiturates, stimulants, hypnotics and illicit drugs.

Further, sample collection of oral fluid from post-mortem subjects and from live and post-mortem animals in accordance with the present invention demonstrates the surprising sensitivity of this collection method in detecting drugs of interest. Our methodology using oral fluid was shown to be about three times more effective in detecting drugs of interest qualitatively compared to the use of conventional matrices such as blood, urine, bile, and liver tissue, as shown by the results obtained by Lab X. Thus, the present invention using oral fluid collection provides a surprisingly sensitive method for qualitative analysis of samples from post-mortem subjects and from live and post-mortem animals. The results of the qualitative drug screening in accordance with the invention then can be further confirmed and quantified utilizing analytical instrumentation.

After qualitative analysis of the post-mortem samples, oral samples were analyzed from the post-mortem subjects and from live and post-mortem animals utilizing LC-MS/MS instrumentation to confirm and quantitate concentrations of the analytes initially detected. This is in contrast to quantitative analyses performed by laboratories using conventional matrices for drug analysis, where various instrumentations are required to quantitate, as well as screen, drug samples collected from these matrices. Comparison of the instrumentations used in the present invention using oral fluid, and that used by Lab X using conventional matrices, for both qualitative and quantitative analyses, is shown in Table 24.

It should be noted that the present invention is not limited to the instrumentation disclosed herein (i.e., ELISA and LC-MS/MS), but includes any suitable instrumentation capable of screening for and quantifying analytes in post-mortem subjects.

TABLE 24

Instrumentation Used by Our Laboratory Compared to Lab X

| Decedent ID | Our Instrumentation | Lab X Instrumentation |
|---|---|---|
| PM-1 | ELISA, LC-MS/MS | LC-MS/MS, GC/MS, GC, EIA, ELISA, LC/TOF-MS |
| PM-2 | ELISA, LC-MS/MS | LC/TOF-MS, HPLC, GC/MS, LC-MS/MS, EIA, ELISA, GC |
| PM-3 | ELISA, LC-MS/MS | LC-MS/MS, GC-GC-GC/MS, GC/MS, LC/TOF-MS, GC |
| PM-4 | ELISA, LC-MS/MS | LC-MS/MS, ELISA, GC, LC/TOF-MS |
| PM-5 | ELISA, LC-MS/MS | LC-MS/MS, GC-GC-GC/MS, HPLC, ELISA, GC, LC/TOF-MS |
| PM-6 | ELISA, LC-MS/MS | GC-GC-GC/MS, LC-MS/MS, EIA, ELISA, GC, LC/TOF-MS |
| PM-7 | ELISA, LC-MS/MS | LC-MS/MS, ELISA, GC, LC/TOF-MS |
| PM-8 | ELISA, LC-MS/MS | LC-MS/MS, GC-GC-GC/MS, GC, EIA, ELISA, LC/TOF-MS |
| PM-9 | ELISA, LC-MS/MS | LC-MS/MS, GC/MS, HPLC, EIA, ELISA, GC, LC/TOF-MS |
| PM-10 | ELISA, LC-MS/MS | GC-GC-GC/MS, GC/MS, LC-MS/MS, EIA, ELISA, GC, LC/TOF-MS |
| PM-11 | ELISA, LC-MS/MS | GC-GC-GC/MS, GC/MS, LC-MS/MS, EIA, ELISA, LC/TOF-MS, GC |
| PM-12 | ELISA, LC-MS/MS | GC-GC-GC/MS, GC/MS, LC-MS/MS, ELISA, GC, LC/TOF-MS |
| PM-13 | ELISA, LC-MS/MS | LC-MS/MS, GC-GC-GC/MS, GC, ELISA, C |
| PM-14 | ELISA, LC-MS/MS | GC/MS, HPLC, LC-MS/MS, GC, C, ELISA |
| PM-15 | ELISA, LC-MS/MS | LC-MS/MS, GC, ELISA, LC/TOF-MS, EIA |
| PM-16 | LC-MS/MS | N/A |
| PM-17 | LC-MS/MS | EIA, GC, LCMS |
| PM-18 | LC-MS/MS | GC/MS |
| PM-19 | LC-MS/MS | N/A |
| PM-20 | LC-MS/MS | GC |

Correlation and t-Test Statistics

Correlation statistics were calculated to analyze the data gathered by our laboratory and Lab X, and are shown in Table 25.*

TABLE 25

Correlation and Comparison Statistics for Sublingual and Lab X Samples (ng/mL)

| Decedent ID | Mean | Variance | Lab X Mean | Lab X Variance | Degrees of Freedom (df) | Sample Correlation Coefficient (r) | P-value |
|---|---|---|---|---|---|---|---|
| PM-1 | 343.03 | 314,741.43 | 180.00 | 12,0486.50 | 7 | 0.393 | 0.598 |
| PM-2 | 478.38 | 1,188,492.02 | 872.50 | 4,095,437.50 | 8 | 0.278 | 0.686 |
| PM-3 | 182.75 | 61,274.74 | 293.83 | 410,472.17 | 6 | 0.533 | 0.706 |
| PM-4 | 17,624.49 | 253,428,848.19 | 73.63 | 11,978.80 | 2 | 0.441 | 0.196 |
| PM-5 | 1.74 | 3.94 | 6.80 | 9.68 | 2 | 0.342 | 0.192 |
| PM-6 | 42.43 | 425.01 | 20.67 | 321.33 | 4 | 0.880 | 0.240 |

TABLE 25-continued

Correlation and Comparison Statistics for Sublingual and Lab X Samples (ng/mL)

| Decedent ID | Mean | Variance | Lab X Mean | Lab X Variance | Degrees of Freedom (df) | Sample Correlation Coefficient (r) | P-value |
|---|---|---|---|---|---|---|---|
| PM-7 | N/A | N/A | N/A | N/A | N/A | 0.095 | N/A |
| PM-8 | 55.91 | 3,582.17 | 81.80 | 11,941.20 | 6 | 0.848 | 0.659 |
| PM-9 | 1,179.84 | 2,349,418.07 | 305.00 | 186,050.00 | 1 | 0.260 | 0.579 |
| PM-10 | 10.01 | 358.18 | 20.53 | 579.23 | 9 | 0.649 | 0.422 |
| PM-11 | 197.29 | 179,842.61 | 224.20 | 239,778.20 | 8 | 0.264 | 0.928 |
| PM-12 | 35.69 | 2,335.83 | 89.67 | 38,561.87 | 6 | 0.517 | 0.538 |
| PM-13 | N/A | N/A | N/A | N/A | N/A | 0.228 | N/A |
| PM-14 | 34.89 | 2,051.28 | 183.33 | 46,233.33 | 34.89 | 0.400 | 0.363 |
| PM-15 | 78.47 | 944.18 | 37.67 | 1,196.33 | 4 | 0.906 | 0.201 |
| PM-16 | N/A | N/A | N/A | N/A | N/A | N/A | N/A |
| PM-17 | N/A | N/A | N/A | N/A | N/A | N/A | N/A |
| PM-18 | N/A | N/A | N/A | N/A | N/A | N/A | N/A |
| PM-19 | N/A | N/A | N/A | N/A | N/A | N/A | N/A |
| PM-20 | N/A | N/A | N/A | N/A | N/A | N/A | N/A |

N/A (Not Applicable)
*PM-16 to PM-20 not subjected to statistical analysis because of inability of Lab X to quantify any concentration of drugs or drug metabolites in these subjects.

The mean and variance calculated for our results were for the sublingual location only. The mean and variance calculated for Lab X results were for all matrices reported. All fifteen post-mortem samples showed a positive correlation between the data collected by our laboratory and Lab X. This indicates a direct relationship between the two sets of data (i.e., if one set increases, the other set increases). As shown in Table 10, statistics (t-test) were utilized for data comparison. An important finding was that concentration levels were not equivalent between our laboratory and Lab X, as our methodology resulted in higher concentrations (i.e., was more sensitive) in most cases.

P-values were calculated by our laboratory to determine the probability of rejection of the test hypothesis that oral fluid and blood are directly related to each other. Because the p-values for all decedent samples were greater than 0.05 ($p>0.05$), the testing hypothesis could not be rejected, which definitively showed that oral fluid and blood sampling are directly and proportionately related to one another, confirming that oral fluid is a viable alternative to conventional methods of sampling. Further, the results from our laboratory using oral fluid samples, when compared the results from Lab X, confirms that not only is oral fluid a viable alternative, but indeed a superior alternative, being faster, sensitive, more consistent, and less invasive than conventional methods.

Conclusion

This study demonstrated that oral fluid collected from various sites is not only an equivalent, but a superior, alternative to traditional methods of fluid and tissue collections for post-mortem drug analysis subjects and from live and post-mortem animals, due to the ease of collection, simpler use of instrumentation, safety concerns, and rapidity and quality of results obtained. Because conventional post-mortem analyses are performed mainly with blood as the matrix, drug concentrations often may vary in unpredictable ways based upon the collection site of the blood, time of sampling, and the phenomenon of redistribution. The sampling compartment is assumed to relate to the concentration at the site of action. After death, however, compartments are usually altered as the integrity of the compartmental barriers is lost. This, in turn, may alter the concentration of one or more drugs originally contained in the intact compartments, leading to erroneous drug testing results (i.e., either the non-finding of a particular drug in a particular matrix), or the finding of lowered or skewed concentration levels. In contrast, the use of oral fluid as the primary analytical matrix for post-mortem drug testing eliminates these error factors, as oral fluid is seen to be surprisingly preserved after death in all the sites in which oral fluid may be collected. In other words, the sites reported herein in which oral fluid was collected appear to serve as intact reservoirs for oral fluid, so that any drugs contained in the oral fluid are able to be analyzed with enhanced sensitivity, consistency and accuracy compared to conventional methodologies. In addition, the use of oral fluid to detect and quantify non-naturally occurring drugs in live animals is much less stressful to animals compared to the invasive method of using blood as the matrix.

The ease of collection eliminates the necessity to collect additional fluids and tissue, and thus accelerates the autopsy process, which allows for cases to be closed substantially faster, as, for example, examination of larvae and entomological samples associated with putrefied cases may cause increased expense and time to determine cause of death. This study demonstrates that oral fluid can be collected rapidly and easily by procedures that do not interfere with medical examination and that are less time consuming relative to the collection procedures associated with blood, urine, bile, and other fluids. Further, the use of oral fluid samples requires only one screening and analytical technique. This is in contrast to conventional methods which require the use of numerous matrices, as well as numerous screening and analytical techniques. Thus, because the methodology of the present invention requires the use of only one matrix (i.e., oral fluid) and two instrumentalities to obtain sensitive and consistent results, the results can be reported significantly faster than conventional methods using conventional matrices and requiring the use of a number of instruments.

EXAMPLES

The present invention is more particularly described in the following non-limiting examples, which are intended to be illustrative only, as numerous modifications and variations therein will be apparent to those skilled in the art.

The following two examples report forensic toxicology results on a 62-year old female decedent weighing 145 pounds suspected of dying from a drug overdose, using the methodology of the present invention.

Example 1—Oral Fluid Collection from Sublingual Area

A cellulose collection pad from a Quantisal Saliva Collection Device was placed into the sublingual area adjacent to the second bicuspid and first molar in the buccal cavity of the decedent for approximately three to five minutes. The collection pad was removed and observed for saturation of the pad with oral fluid. The collection pad was placed into the collection device, containing a non-azide buffer. The coroner's ID for the subject, date, and sample location was written onto the collection device and placed into a dual-pocketed zippered biohazard bag. The collection device was placed into the zippered pocket of the bag and the chain of custody was folded and placed into the opposing pocket. All samples were placed into a United Parcel Services Laboratory (UPS) Pak and then shipped to the laboratory for analyses. Upon receipt in the laboratory, the sample was inspected for viability, sufficient quantity of oral fluid, and paperwork. The samples were prepared under a negative pressure hood and filtered using a blood serum filter (16 mm×4 inches).

Qualitative results were derived using a Direct ELISA kit (96-well microplate), which is based upon the competitive binding to antibody of enzyme-labeled antigen and unlabeled antigen in proportion to their concentration in the reaction mixture. Samples and calibrators were prepared by pipetting 750 μL into labeled 12×75 mm disposable glass culture tubes (Fisher Scientific). Calibrators were prepared in duplicate (negative, low, cut-off, and high). Qualitative results were completed in approximately three hours and compiled for reporting to the coroner's office.

Quantitative results were completed using a 6460 LC-MS/MS. The results then were reviewed twice by a laboratory scientist and reported to the coroner's office within approximately two to five days upon receipt of the sample. The following drugs and their concentrations were detected in the sublingual region: 6-acetylmorphine, 109.69 ng/mL; benzoylecgonine, 669.59 ng/mL; carisoprodol, 49.20 ng/mL; codeine, 5.64 ng/mL; fentanyl, 70.62 ng/mL; and morphine, 197.42 ng/mL. The results were compared to forensic toxicology results detected in blood of the same decedent by Lab X.

The results obtained with oral fluid collected from the sublingual region of the subject were found to be substantially similar to or superior with respect to the number of drugs detected qualitatively and concentrations of the drugs detected quantitatively compared to results obtained from blood collected from the same decedent by Lab X.

Example 2—Oral Fluid Collection from Submandibular Gland

During the initial autopsy preparation procedure, an incision dissection was made to expose the submandibular gland of the decedent. An incision then was made in the gland and a cellulose collection pad from a Quantisal Saliva Collection Device was inserted into the gland for approximately five to ten minutes. The collection pad was removed and observed for saturation of the pad with oral fluid. The collection pad was placed into the collection device containing a non-azide buffer. The coroner's ID for the subject, date, and sample location was written onto the collection device and placed into a dual-pocketed zippered biohazard bag. The collection device was placed into the zippered pocket of the bag and the chain of custody was folded and placed into the opposing pocket. All samples were placed into a UPS Laboratory Pak and then shipped to the laboratory for analyses. Upon receipt into the laboratory, the sample was observed for viability, sufficient oral fluid quantity, and paperwork. The samples were prepared under a negative pressure hood and filtered using a blood serum filter (16 mm×4 inches).

Qualitative results were derived using a Direct ELISA kit (96-well microplate), which is based upon the competitive binding to antibody of enzyme-labeled antigen and unlabeled antigen in proportion to their concentration in the reaction mixture. Samples and calibrators were prepared by pipetting 750 μL into labeled 12×75 mm disposable glass culture tubes (Fisher Scientific). Calibrators were prepared in duplicate (negative, low, cut-off, and high). Qualitative results were completed in approximately 3 hours and compiled for reporting to the coroner's office.

Quantitative results were completed using a 6460 LC-MS/MS. The results then were reviewed twice by a laboratory scientist and reported to the coroner's office within approximately 24 to 72 hours upon receipt of the sample. The following drugs and their concentrations were detected in the submandibular gland: 6-acetylmorphine, 0.0 ng/mL; benzoylecgonine, 269.02 ng/mL; carisoprodol, 54.38 ng/mL; codeine, 0.0 ng/mL; fentanyl, 11.41 ng/mL; and morphine, 12.34 ng/mL. The results were compared to forensic toxicology results detected in blood of the same decedent by Lab X.

The results obtained with oral fluid collected from the submandibular gland of the subject were found to be substantially similar to or superior with respect to the number of drugs detected qualitatively and concentrations of the drugs detected quantitatively compared to results obtained from blood collected from the same decedent by Lab X.

Example 3—Oral Fluid Collection from Sublingual Area of a Live Dog

Sedation of the dog with 30 mg/kg pentobarbital administered intravenously preceded the collection procedure. A cellulose collection pad from a Quantisal Saliva Collection Device was placed into the sublingual area adjacent to the second bicuspid and first molar in the buccal cavity of the dog for three minutes. The collection pad was removed and observed for saturation of the pad with oral fluid. The collection pad was placed into the collection device, containing a non-azide buffer. The ID for the subject, date, and sample location was written onto the collection device and placed into a dual-pocketed zippered biohazard bag. The collection device was placed into the zippered pocket of the bag and the chain of custody was folded and placed into the opposing pocket. All samples were placed into a United Parcel Services Laboratory (UPS) Pak and then shipped to the laboratory for analyses. Upon receipt in the laboratory, the sample was inspected for viability, sufficient quantity of oral fluid, and paperwork. The samples were prepared under a negative pressure hood and filtered using a blood serum filter (16 mm×4 inches).

Quantitative results were completed using a 6460 LC-MS/MS. The results then were reviewed twice by a laboratory scientist and reported back to our laboratory within four hours. The following drug was detected and quantified in the sublingual region: ketamine, 598.30 mL.

Example 4—Oral Fluid Collection from Sublingual Area of a Post-Mortem Dog

A cellulose collection pad from a Quantisal Saliva Collection Device was placed into the sublingual area adjacent to the second bicuspid and first molar in the buccal cavity of the dog for three minutes. The collection pad was removed and observed for saturation of the pad with oral fluid. The collection pad was placed into the collection device, containing a non-azide buffer. The ID for the subject, date, and sample location was written onto the collection device and placed into a dual-pocketed zippered biohazard bag. The collection device was placed into the zippered pocket of the bag and the chain of custody was folded and placed into the opposing pocket. All samples were placed into a United Parcel Services Laboratory (UPS) Pak and then shipped to the laboratory for analyses. Upon receipt in the laboratory, the sample was inspected for viability, sufficient quantity of oral fluid, and paperwork. The samples were prepared under a negative pressure hood and filtered using a blood serum filter (16 mm×4 inches).

Quantitative results were completed using a 6460 LC-MS/MS. The results then were reviewed twice by a laboratory scientist and reported back to our laboratory within four hours. The following drugs were detected and quantified in the sublingual region: diazepam, 4.00 ng/mL; ketamine, 408.30 ng/mL; acetaminophen, 12.20 ng/mL; tramadol, 49.70 ng/mL; and gabapentin, 205.00 ng/mL.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A rapid, sensitive method for the detection and quantification of non-naturally occurring drugs for forensic drug testing in a post-mortem, mammalian non-human animal using oral fluid from the post-mortem, mammalian non-human animal, comprising:

collecting a sample of oral fluid from a post-mortem, mammalian non-human animal, wherein the sample of oral fluid that is collected is about 1 milliliter (ml);

analyzing the sample of oral fluid quantitatively using a Liquid Chromatography-Mass Spectrometry/Mass Spectrometry (LC-MS/MS) method to determine concentration of the one or more non-naturally occurring drugs from the post-mortem, mammalian non-human animal; and identifying the one or more non-naturally occurring drugs from the post-mortem, mammalian non-human animal, wherein detection and quantification in oral fluid is more rapid and sensitive than quantification of the non-naturally occurring drugs in a biological sample selected from the group consisting of urine, blood, bile and liver tissue from the post-mortem, mammalian non-human animal using the same LC-MS/MS method, wherein the one or more non-naturally occurring drugs are selected from the group consisting of acetaminophen, 6-acetylmorphine, alprazolam, amphetamine, benzoylecgonine, buprenorphine, carisoprodol, cis-tramadol, clonazepam, cocaine/benzoylecgonine, codeine, clonazepam, cyclobenzaprine, o-desmethyloxycodone, diazepam, ethyl glucuronide, ethyl sulfate, fentanyl, gabapentin, hydrocodone, hydromorphone, ketamine, lorazepam, meperidine, methadone, 3,4-methamphetamine, methylenedioxy-methamphetamine (MDMA), methylphenidate, midazolam, morphine, naloxone, naltrexone, o-desmethyl-cis-tramadol, oxazepam, oxycodone, oxymorphone, phencyclidine (PCP), propoxyphene, quetiapine, tapentadol, temazepam, delta-9-tetrahydrocannabinol (THC), tramadol and triazolam, and wherein quantitative results are obtained in as soon as three hours.

2. The method of claim 1, wherein the sample of oral fluid is collected from a buccal cavity of the post-mortem, mammalian non-human animal.

3. The method of claim 2, wherein the sample of oral fluid is collected from a sublingual region of the buccal cavity.

4. The method of claim 1, wherein the sample of oral fluid is collected from a submandibular gland.

5. The method of claim 1, wherein the sample of oral fluid is collected with a collection pad in about one minute to about ten minutes.

6. The method of claim 1, wherein the post-mortem, mammalian non-human animal is selected from the group consisting of dogs, cats, horses and farm animals.

7. The method of claim 6, wherein the post-mortem, mammalian non-human animal is a dog.

* * * * *